(12) United States Patent
Batchelor et al.

(10) Patent No.: US 10,898,260 B2
(45) Date of Patent: Jan. 26, 2021

(54) RECONFIGURABLE ELECTROSURGICAL DEVICE

(71) Applicant: GYRUS ACMI, INC., Southborough, MA (US)

(72) Inventors: Kester J. Batchelor, Mound, MN (US); Richard J. Curtis, Maple Grove, MN (US); Ryan J. Windgassen, Nowthen, MN (US)

(73) Assignee: Gyrus Acmi, Inc., Southborough, MA (US)

( * ) Notice: Subject to any disclaimer, the term of this patent is extended or adjusted under 35 U.S.C. 154(b) by 0 days.

(21) Appl. No.: 16/219,197

(22) Filed: Dec. 13, 2018

(65) Prior Publication Data

US 2019/0201078 A1 Jul. 4, 2019

Related U.S. Application Data

(63) Continuation of application No. 14/830,069, filed on Aug. 19, 2015, now Pat. No. 10,182,861.
(Continued)

(51) Int. Cl.
*A61B 17/295* (2006.01)
*A61B 18/14* (2006.01)
(Continued)

(52) U.S. Cl.
CPC ...... *A61B 18/1442* (2013.01); *A61B 17/2812* (2013.01); *A61B 17/2833* (2013.01);
(Continued)

(58) Field of Classification Search
CPC .............. A61B 18/1442; A61B 18/085; A61B 2018/00607; A61B 2018/00601;
(Continued)

(56) References Cited

U.S. PATENT DOCUMENTS

| 1,089,664 A | 3/1914 | Osada |
|---|---|---|
| 1,198,958 A | 9/1916 | Risely |

(Continued)

FOREIGN PATENT DOCUMENTS

| CN | 1149519 A | 5/1997 |
|---|---|---|
| CN | 101843523 A | 9/2010 |

(Continued)

OTHER PUBLICATIONS

315MHZ sliding remote cover, available at website : http://www.aliexpress.com/item/Sliding-Cover-Gate-Remote-Control-Duplicator-Adjustable-Frequency-Remote-Copy-100pCS-lot-Free-Shipping-by-DHL/566451354.html?tracelog=back_to_detail_a (accessed on Feb. 21, 2013).

(Continued)

*Primary Examiner* — Thomas A Giuliani
(74) *Attorney, Agent, or Firm* — Schwegman Lundberg & Woessner, P.A.

(57) ABSTRACT

A device comprising: a a pair of arms; a blade; and a blade extending mechanism including detent positions where the blade is locked into a position related to each of the detent positions. The device is capable of switching between: a configuration where the arms are free to move towards each other, and the blade is locked into a position related to a first one of the detent positions; a configuration where the arms are secured together by a securing mechanism that prevents movement of the arms towards each other; and a configuration where the arms are secured together so that the arms are prevented from moving towards each other, and the blade is locked into a position related to a second one of the detent positions so that the blade is substantially flush with or extends beyond a distal end of the arms.

20 Claims, 3 Drawing Sheets

Related U.S. Application Data

(60) Provisional application No. 62/039,506, filed on Aug. 20, 2014.

(51) Int. Cl.
    *A61B 17/28*    (2006.01)
    *A61B 18/08*    (2006.01)
    *A61B 18/12*    (2006.01)
    *A61B 17/00*    (2006.01)
    *A61B 18/00*    (2006.01)

(52) U.S. Cl.
    CPC .......... *A61B 17/295* (2013.01); *A61B 18/085* (2013.01); *A61B 18/1206* (2013.01); *A61B 18/1402* (2013.01); *A61B 17/282* (2013.01); *A61B 2017/00411* (2013.01); *A61B 2018/00273* (2013.01); *A61B 2018/00589* (2013.01); *A61B 2018/00601* (2013.01); *A61B 2018/00607* (2013.01); *A61B 2018/00946* (2013.01); *A61B 2018/00958* (2013.01); *A61B 2018/126* (2013.01); *A61B 2018/1253* (2013.01); *A61B 2018/146* (2013.01); *A61B 2018/1412* (2013.01); *A61B 2018/1455* (2013.01); *A61B 2018/1462* (2013.01)

(58) Field of Classification Search
    CPC .... A61B 2018/0063; A61B 2018/1452; A61B 2018/1455; A61B 2018/1462; A61B 2018/00946; A61B 2018/00958; A61B 2017/2845; A61B 2017/2946; A61B 2017/2837; A61B 17/28; A61B 17/282; A61B 17/2833; A61B 17/29; A61B 17/2841; A61B 17/285; A61B 17/295; A61B 17/30; A61B 17/32; A61B 17/2812
    USPC ............... 606/41, 50–52, 205–207
    See application file for complete search history.

(56) References Cited

U.S. PATENT DOCUMENTS

| | | |
|---|---|---|
| 2,042,985 A | 6/1936 | Gardella |
| 2,214,984 A | 9/1940 | Bachmann |
| 2,381,084 A | 8/1945 | Slad |
| 2,575,652 A | 11/1951 | Bovee |
| 2,894,424 A | 7/1959 | Vaughan |
| 3,399,583 A | 9/1968 | Hall |
| 3,417,752 A | 12/1968 | Butler |
| 3,465,621 A | 9/1969 | Ladd |
| 3,576,072 A | 4/1971 | Foster |
| 3,643,663 A | 2/1972 | Sutter |
| 3,685,518 A | 8/1972 | Beuerle et al. |
| 3,699,632 A | 10/1972 | Anhalt |
| 3,818,784 A | 6/1974 | McClure |
| 3,913,586 A | 10/1975 | Baumgarten |
| 4,041,952 A | 8/1977 | Morrison, Jr. et al. |
| 4,154,226 A | 5/1979 | Hennig et al. |
| 4,171,700 A | 10/1979 | Farin |
| 4,202,337 A | 5/1980 | Hren et al. |
| 4,318,313 A | 3/1982 | Tartaglia |
| 4,375,218 A | 3/1983 | DiGeronimo |
| 4,407,069 A | 10/1983 | Conners |
| 4,418,692 A | 12/1983 | Guay |
| 4,443,935 A | 4/1984 | Zamba et al. |
| 4,463,759 A | 7/1984 | Garito et al. |
| 4,492,231 A | 1/1985 | Auth |
| 4,492,832 A | 1/1985 | Taylor |
| 4,494,543 A | 1/1985 | Hart |
| 4,504,707 A | 3/1985 | Ochiai |
| 4,524,648 A | 6/1985 | Chung |
| 4,552,143 A | 11/1985 | Lottick |
| 4,655,215 A | 4/1987 | Pike |
| 4,669,470 A | 6/1987 | Brandfield |
| 4,686,980 A | 8/1987 | Williams et al. |
| 4,713,885 A | 12/1987 | Keklak et al. |
| 4,757,612 A | 7/1988 | Peyrot |
| 4,784,136 A | 11/1988 | Klein |
| 4,860,745 A | 8/1989 | Farin et al. |
| 4,896,661 A | 1/1990 | Bogert et al. |
| 4,935,027 A | 6/1990 | Yoon |
| 5,021,616 A | 6/1991 | Hardt |
| 5,035,695 A | 7/1991 | Weber, Jr. et al. |
| 5,071,426 A | 12/1991 | Dolgin et al. |
| 5,104,397 A | 4/1992 | Vasconcelos et al. |
| 5,108,392 A | 4/1992 | Spingler |
| 5,147,378 A | 9/1992 | Markham |
| 5,176,702 A | 1/1993 | Bales et al. |
| 5,190,541 A | 3/1993 | Abele et al. |
| 5,196,009 A | 3/1993 | Kirwan, Jr. |
| 5,207,691 A | 5/1993 | Nardella |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,293,878 A | 3/1994 | Bales et al. |
| 5,318,589 A | 6/1994 | Lichtman |
| 5,342,359 A | 8/1994 | Rydell |
| 5,370,659 A | 12/1994 | Sakashita |
| 5,403,312 A | 4/1995 | Yates et al. |
| 5,413,575 A | 5/1995 | Haenggi |
| 5,423,814 A | 6/1995 | Zhu et al. |
| 5,425,743 A | 6/1995 | Nicholas |
| 5,440,813 A | 8/1995 | Roskam |
| 5,441,498 A | 8/1995 | Perkins |
| 5,443,463 A | 8/1995 | Stern et al. |
| 5,456,695 A | 10/1995 | Herve Dellemagne |
| 5,458,598 A | 10/1995 | Fienberg et al. |
| 5,472,442 A | 12/1995 | Klicek |
| 5,483,952 A | 1/1996 | Aranyi |
| 5,484,435 A | 1/1996 | Fleenor et al. |
| 5,499,998 A | 3/1996 | Meade |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,626,578 A | 5/1997 | Tihon |
| 5,658,281 A | 8/1997 | Heard |
| 5,661,100 A | 8/1997 | Minami et al. |
| 5,665,100 A | 9/1997 | Yoon |
| 5,693,052 A | 12/1997 | Weaver |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| 5,810,805 A | 9/1998 | Sutcu et al. |
| 5,827,281 A | 10/1998 | Levin |
| 5,884,954 A | 3/1999 | Trozera |
| 5,891,140 A | 4/1999 | Ginn et al. |
| 5,902,301 A | 5/1999 | Olig |
| 5,922,001 A | 7/1999 | Yoon |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,050,996 A | 4/2000 | Schmaltz et al. |
| 6,053,908 A | 4/2000 | Crainich et al. |
| 6,074,386 A | 6/2000 | Goble et al. |
| 6,102,909 A | 8/2000 | Chen et al. |
| 6,110,171 A | 8/2000 | Rydell |
| 6,113,596 A | 9/2000 | Hooven et al. |
| 6,117,158 A | 9/2000 | Measamer et al. |
| 6,117,169 A | 9/2000 | Moe |
| 6,152,923 A | 11/2000 | Ryan |
| 6,190,386 B1 | 2/2001 | Rydell |
| 6,270,497 B1 | 8/2001 | Sekino et al. |
| 6,273,887 B1 | 8/2001 | Yamauchi et al. |
| 6,325,795 B1 | 12/2001 | Lindemann et al. |
| 6,355,032 B1 | 3/2002 | Hovda et al. |
| 6,358,268 B1 | 3/2002 | Hunt et al. |
| 6,402,747 B1 | 6/2002 | Lindemann et al. |

(56) References Cited

U.S. PATENT DOCUMENTS

| | | |
|---|---|---|
| 6,428,538 B1 | 8/2002 | Blewett et al. |
| 6,458,128 B1 | 10/2002 | Schulze |
| 6,464,704 B2 | 10/2002 | Schmaltz et al. |
| 6,486,419 B2 | 11/2002 | Horiguchi et al. |
| 6,494,886 B1 | 12/2002 | Wilk et al. |
| 6,514,252 B2 | 2/2003 | Nezhat et al. |
| 6,551,313 B1 | 4/2003 | Levin |
| 6,554,829 B2 | 4/2003 | Schulze et al. |
| 6,585,735 B1 | 7/2003 | Frazier et al. |
| 6,619,038 B2 | 9/2003 | Takada et al. |
| 6,623,499 B1 | 9/2003 | Andreini et al. |
| 6,641,595 B1 | 11/2003 | Moran et al. |
| 6,652,514 B2 | 11/2003 | Ellman et al. |
| 6,679,882 B1 | 1/2004 | Kornerup |
| 6,689,130 B2 | 2/2004 | Arai et al. |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,773,434 B2 | 8/2004 | Ciarrocca |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,108,694 B2 | 9/2006 | Miura et al. |
| 7,112,199 B2 | 9/2006 | Cosmescu |
| 7,147,637 B2 | 12/2006 | Goble |
| 7,147,638 B2 | 12/2006 | Goble |
| 7,150,749 B2 | 12/2006 | Dycus et al. |
| 7,156,846 B2 | 1/2007 | Dycus et al. |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,377,902 B2 | 5/2008 | Burbank |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,625,391 B2 | 12/2009 | Kebel et al. |
| 7,674,261 B2 | 3/2010 | Garito et al. |
| 7,686,827 B2 | 3/2010 | Hushka |
| 7,722,607 B2 | 5/2010 | Dumbauld et al. |
| 7,753,909 B2 | 7/2010 | Chapman et al. |
| 7,758,577 B2 | 7/2010 | Nobis et al. |
| 7,789,878 B2 | 9/2010 | Dumbauld et al. |
| 7,879,035 B2 | 2/2011 | Garrison et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,931,649 B2 | 4/2011 | Couture et al. |
| 7,931,668 B2 | 4/2011 | Sloat |
| 7,938,469 B2 | 5/2011 | Ait-Mani |
| 7,942,872 B2 | 5/2011 | Ein-Gal |
| 7,955,331 B2 | 6/2011 | Truckai et al. |
| 7,998,140 B2 | 8/2011 | McClurken et al. |
| 8,062,292 B1 | 11/2011 | Slater |
| 8,100,894 B2 | 1/2012 | Mucko et al. |
| 8,162,940 B2 | 4/2012 | Johnson et al. |
| 8,216,231 B2 | 7/2012 | Behl et al. |
| 8,226,649 B2 | 7/2012 | Falkenstein et al. |
| 8,246,094 B2 | 8/2012 | Long et al. |
| 8,251,989 B1 | 8/2012 | Newton et al. |
| 8,262,655 B2 | 9/2012 | Ghabrial et al. |
| 8,267,935 B2 | 9/2012 | Couture et al. |
| 8,328,170 B2 | 12/2012 | Wasinger |
| 8,361,065 B2 | 1/2013 | West et al. |
| 8,361,072 B2 | 1/2013 | Dumbauld et al. |
| 8,485,413 B2 | 7/2013 | Scheib et al. |
| 8,491,626 B2 | 7/2013 | Roy et al. |
| 8,496,603 B2 | 7/2013 | Mamourian |
| 8,568,411 B2 | 10/2013 | Falkenstein et al. |
| 8,628,529 B2 | 1/2014 | Aldridge et al. |
| 8,632,553 B2 | 1/2014 | Sakamoto et al. |
| 8,702,691 B2 | 4/2014 | Weber et al. |
| 8,702,700 B2 | 4/2014 | Maeda et al. |
| 8,882,756 B2 | 11/2014 | Greeley et al. |
| 8,939,972 B2 | 1/2015 | Twomey |
| 9,023,035 B2 | 5/2015 | Allen et al. |
| 9,204,879 B2 | 12/2015 | Shelton |
| 9,320,563 B2 | 4/2016 | Brustad et al. |
| 9,326,810 B2 | 5/2016 | Shiley et al. |
| 9,358,065 B2 | 6/2016 | Ladtkow et al. |
| 9,439,665 B2 | 9/2016 | Marczyk et al. |
| 9,452,011 B2 * | 9/2016 | Batchelor .......... A61B 18/1233 |
| 9,707,028 B2 * | 7/2017 | Batchelor .......... A61B 17/2812 |
| 10,182,861 B2 * | 1/2019 | Batchelor .......... A61B 17/2812 |
| 10,456,191 B2 | 10/2019 | Batchelor et al. |
| 2002/0106609 A1 | 8/2002 | Palermo et al. |
| 2002/0107517 A1 | 8/2002 | Witt et al. |
| 2002/0115997 A1 | 8/2002 | Truckai et al. |
| 2002/0173787 A1 | 11/2002 | Buysse et al. |
| 2003/0018329 A1 | 1/2003 | Hooven |
| 2003/0018331 A1 | 1/2003 | Dycus et al. |
| 2003/0144652 A1 | 1/2003 | Baker et al. |
| 2003/0050633 A1 | 3/2003 | Ellman et al. |
| 2003/0097126 A1 | 5/2003 | Woloszko et al. |
| 2003/0105474 A1 | 6/2003 | Bonutti |
| 2003/0109876 A1 | 6/2003 | Yamauchi |
| 2003/0114850 A1 | 6/2003 | McClurken |
| 2003/0181904 A1 | 9/2003 | Levine et al. |
| 2004/0030330 A1 | 2/2004 | Brassell et al. |
| 2004/0082946 A1 | 4/2004 | Malis et al. |
| 2004/0097117 A1 | 5/2004 | Gonnering |
| 2005/0065510 A1 | 3/2005 | Carmel et al. |
| 2005/0113824 A1 | 5/2005 | Sartor et al. |
| 2005/0113825 A1 | 5/2005 | Cosmescu |
| 2005/0113827 A1 * | 5/2005 | Dumbauld .......... A61B 18/1445 606/45 |
| 2005/0159745 A1 | 7/2005 | Truckai et al. |
| 2005/0187512 A1 | 8/2005 | Isola et al. |
| 2005/0216019 A1 | 9/2005 | Eckman |
| 2006/0041257 A1 | 2/2006 | Sartor et al. |
| 2006/0084973 A1 | 4/2006 | Hushka |
| 2006/0089670 A1 | 4/2006 | Hushka |
| 2006/0190035 A1 | 8/2006 | Hushka et al. |
| 2006/0217701 A1 | 9/2006 | Young et al. |
| 2007/0049922 A1 | 3/2007 | Rontal |
| 2007/0078458 A1 | 4/2007 | Dambauld et al. |
| 2007/0093857 A1 | 4/2007 | Campbell |
| 2007/0123855 A1 | 5/2007 | Morley et al. |
| 2007/0129716 A1 | 6/2007 | Daw |
| 2007/0179491 A1 | 8/2007 | Kratoska et al. |
| 2008/0033428 A1 | 2/2008 | Artale et al. |
| 2008/0058845 A1 | 3/2008 | Shimizu et al. |
| 2008/0077129 A1 | 3/2008 | Van Wyk et al. |
| 2008/0147092 A1 | 6/2008 | Rogge et al. |
| 2008/0154300 A1 | 6/2008 | Jabbour |
| 2008/0236860 A1 | 10/2008 | Howe |
| 2008/0287948 A1 | 11/2008 | Newton et al. |
| 2009/0062786 A1 | 3/2009 | Garito et al. |
| 2009/0062792 A1 | 3/2009 | Vakharia et al. |
| 2009/0062830 A1 | 3/2009 | Hiraoka |
| 2009/0093804 A1 | 4/2009 | Newton |
| 2009/0138003 A1 | 5/2009 | DeVille et al. |
| 2009/0138013 A1 | 5/2009 | Thorne et al. |
| 2009/0192509 A1 | 7/2009 | Curtis |
| 2009/0248002 A1 | 10/2009 | Takashino et al. |
| 2010/0042096 A1 | 2/2010 | Ellman |
| 2010/0087814 A1 | 4/2010 | Desinger et al. |
| 2010/0137854 A1 | 6/2010 | Hosier |
| 2010/0228249 A1 | 9/2010 | Mohr |
| 2011/0045680 A1 | 2/2011 | Beller |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2011/0251613 A1 | 10/2011 | Guerra et al. |
| 2011/0301602 A1 * | 12/2011 | Roy ............... A61B 17/29 606/51 |

(56) References Cited

U.S. PATENT DOCUMENTS

| | | | |
|---|---|---|---|
| 2011/0319892 A1 | 12/2011 | Blomeyer | |
| 2012/0022530 A1 | 1/2012 | Woodruff et al. | |
| 2012/0059409 A1* | 3/2012 | Reschke | A61B 17/2833 |
| | | | 606/208 |
| 2012/0078292 A1 | 3/2012 | Banju | |
| 2012/0095460 A1 | 4/2012 | Rooks et al. | |
| 2012/0101501 A1 | 4/2012 | Nishimura et al. | |
| 2012/0123405 A1 | 5/2012 | Moua et al. | |
| 2012/0150165 A1 | 6/2012 | Conley | |
| 2012/0202388 A1 | 8/2012 | Selig | |
| 2013/0023874 A1 | 1/2013 | Lawes et al. | |
| 2013/0066317 A1 | 3/2013 | Evans et al. | |
| 2013/0079762 A1 | 3/2013 | Twomey et al. | |
| 2013/0085516 A1* | 4/2013 | Kerr | A61B 17/295 |
| | | | 606/167 |
| 2013/0138096 A1 | 5/2013 | Benn | |
| 2013/0144284 A1 | 6/2013 | Behnke, II et al. | |
| 2013/0178852 A1 | 7/2013 | Allen, IV et al. | |
| 2013/0237982 A1 | 9/2013 | Rencher et al. | |
| 2013/0296846 A1 | 11/2013 | Canady et al. | |
| 2014/0018795 A1 | 1/2014 | Shilev et al. | |
| 2014/0100569 A1 | 4/2014 | Lawes et al. | |
| 2014/0155701 A1 | 6/2014 | Jayaraj | |
| 2014/0236202 A1 | 8/2014 | Palmer et al. | |
| 2014/0276772 A1 | 9/2014 | Batchelor et al. | |
| 2014/0276785 A1 | 9/2014 | Batchelor et al. | |
| 2014/0276786 A1 | 9/2014 | Batchelor | |
| 2014/0276794 A1 | 9/2014 | Batchelor et al. | |
| 2014/0276795 A1 | 9/2014 | Batchelor et al. | |
| 2014/0276796 A1* | 9/2014 | Batchelor | A61B 18/1233 |
| | | | 606/42 |
| 2014/0276797 A1* | 9/2014 | Batchelor | A61B 18/1233 |
| | | | 606/42 |
| 2014/0276798 A1 | 9/2014 | Batchelor et al. | |
| 2014/0276799 A1 | 9/2014 | Batchelor et al. | |
| 2014/0276800 A1 | 9/2014 | Batchelor et al. | |
| 2014/0276804 A1 | 9/2014 | Batchelor | |
| 2015/0119885 A1* | 4/2015 | Windgassen | A61B 18/1233 |
| | | | 606/42 |
| 2015/0148798 A1* | 5/2015 | Windgassen | A61B 18/1233 |
| | | | 606/42 |
| 2015/0320485 A1 | 11/2015 | Batchelor et al. | |
| 2016/0051273 A1 | 2/2016 | Batchelor et al. | |
| 2016/0051275 A1 | 2/2016 | Batchelor et al. | |
| 2016/0051314 A1 | 2/2016 | Batchelor et al. | |
| 2017/0281260 A1 | 10/2017 | Batchelor et al. | |
| 2020/0008861 A1 | 1/2020 | Batchelor et al. | |

FOREIGN PATENT DOCUMENTS

| | | |
|---|---|---|
| CN | 102164556 | 8/2011 |
| CN | 102836006 | 12/2012 |
| CN | 103429185 A | 12/2013 |
| CN | 105682592 A | 6/2016 |
| CN | 106659534 A | 5/2017 |
| CN | 105682592 B | 3/2018 |
| CN | 108186111 A | 6/2018 |
| CN | 106659534 B | 3/2020 |
| EP | 0392548 A1 | 10/1994 |
| EP | 0392548 B1 | 10/1994 |
| EP | 1089664 | 4/2001 |
| EP | 1769765 A1 | 4/2007 |
| EP | 1530952 A1 | 7/2007 |
| EP | 1810629 A1 | 7/2007 |
| EP | 1977706 A1 | 10/2008 |
| EP | 2345454 A1 | 7/2011 |
| EP | 2403422 | 1/2012 |
| EP | 2449992 A1 | 5/2012 |
| EP | 3052041 A1 | 8/2016 |
| EP | 3134019 A1 | 3/2017 |
| EP | 3052041 B1 | 4/2017 |
| EP | 3195821 A2 | 7/2017 |
| EP | 3335656 A1 | 6/2018 |
| EP | 3195821 B1 | 5/2019 |
| EP | 3335656 B1 | 6/2019 |
| JP | S50143380 U | 11/1975 |
| JP | H10-137259 A | 5/1998 |
| JP | H10-504485 A | 5/1998 |
| JP | 11169381 A | 6/1999 |
| JP | H11-169381 A | 6/1999 |
| JP | 2000070280 A | 3/2000 |
| JP | 2000210301 A | 8/2000 |
| JP | 2001029353 A | 2/2001 |
| JP | 2001170070 A | 6/2001 |
| JP | 2004508875 A | 3/2004 |
| JP | 2005144192 A | 6/2005 |
| JP | 2005521465 A | 7/2005 |
| JP | 2006-000322 A | 1/2006 |
| JP | 2006-326157 A | 12/2006 |
| JP | 2009247893 A | 10/2009 |
| JP | 2011206554 A | 10/2011 |
| JP | 2012518490 A | 8/2012 |
| JP | 2017500968 A | 1/2017 |
| JP | 2017522116 A | 8/2017 |
| JP | 6239129 B2 | 11/2017 |
| JP | 6448762 B2 | 12/2018 |
| WO | WO-9525471 A2 | 9/1995 |
| WO | 96/005776 A1 | 2/1996 |
| WO | 9966850 | 12/1999 |
| WO | 02/24089 A1 | 3/2002 |
| WO | WO-2005060849 A1 | 7/2005 |
| WO | 2006/122279 | 11/2006 |
| WO | 2007/002545 | 1/2007 |
| WO | 2007/093857 | 8/2007 |
| WO | 2010/101897 | 9/2010 |
| WO | 2012/053530 A | 4/2012 |
| WO | 2014/096815 A2 | 6/2014 |
| WO | WO-2016028835 A1 | 2/2016 |
| WO | WO-2016028867 A1 | 2/2016 |
| WO | WO-2016028882 A1 | 2/2016 |

OTHER PUBLICATIONS

Potentially related U.S. Appl. No. 14/589,482, filed Jan. 5, 2015 published as 2015/0148798 on May 28, 2015.

Potentially related U.S. Appl. No. 14/589,515, filed Jan. 5, 2015, published as 2015/0119885 on Apr. 30, 2015.

Potentially related U.S. Appl. No. 14/829,725, filed Aug. 19, 2015.

Potentially related U.S. Appl. No. 14/830,255, filed Aug. 19, 2015.

Potentially related U.S. Appl. No. 14/177,780, filed Feb. 11, 2014, published as 2014/0276794 on Sep. 18, 2014.

Potentially related U.S. Appl. No. 14/178,411, filed Feb. 12, 2014, published as 2014/0276785 on Sep. 18, 2014.

Potentially related U.S. Appl. No. 14/178,569, filed Feb. 12, 2014, published as 2014/0276804 on Sep. 18, 2014.

Potentially related U.S. Appl. No. 14/178,577, filed Feb. 12, 2014, published as 2014/0276786 on Sep. 18, 2014.

Potentially related U.S. Appl. No. 14/205,598, filed Mar. 12, 2014, published as 2014/0276795 on Sep. 18, 2014.

Potentially related U.S. Appl. No. 14/205,919, filed Mar. 12, 2014 published as 2014/0276796 on Sep. 18, 2014.

Potentially related U.S. Appl. No. 14/209,071, filed Mar. 13, 2014 published as 2014/0276798 on Sep. 18, 2014.

Potentially related U.S. Appl. No. 14/210,535, filed Mar. 14, 2014, published as 2014/0276799 on Sep. 18, 2014.

Potentially related U.S. Appl. No. 14/210,741, filed Mar. 14, 2014, published as 2014/0276800 on Sep. 18, 2104.

Potentially related U.S. Appl. No. 14/211,042, filed Mar. 14, 2014, published as 2014/0276772 on Sep. 18, 2014.

Potentially related to U.S. Appl. No. 14/206,010, filed Mar. 12, 2014, published as 2014/0276797 on Sep. 18, 2014.

Sliding Gate Remote Control Duplicator, available at website: http://www.aliexpress.com/item/315MHZ-sliding-cover-remote-controller-duplicating-remote-controller-sliding-gate-remote-garager-door-remote/491795542.html (accessed on Feb. 21, 2013).

International Search Report and Written Opinion for Application No. PCT/US2015/045850 dated Nov. 4, 2015.

Japanese Office Action for Japanese Patent Application No. 2017-502987, dated Dec. 6, 2017.

(56) References Cited

OTHER PUBLICATIONS

Office Action from the Japanese Patent Office for App. No. 2017-502987 dated Jun. 19, 2018.
Office Action from the Chinese National Intellectual Property Administration of Application No. 201580039499.X dated Sep. 30, 2018.
"U.S. Appl. No. 14/830,069, Applicant's Summary of Examiner Interview filed Aug. 23, 2018", 4 pgs.
"U.S. Appl. No. 14/830,069, Examiner Interview Summary dated May 3, 2018", 3 pgs.
"U.S. Appl. No. 14/830,069, Non Final Office Action dated Jan. 30, 2018", 17 pgs.
"U.S. Appl. No. 14/830,069, Notice of Allowance dated Sep. 21, 2018", 14 pgs.
"U.S. Appl. No. 14/830,069, Response filed Apr. 30, 2018 to Non Final Office Action dated Jan. 30, 2018", 14 pgs.
"U.S. Appl. No. 14/830,255, Examiner Interview Summary dated Feb. 24, 2017", 3 pgs.
"U.S. Appl. No. 14/830,255, Non Final Office Action dated Nov. 25, 2016", 13 pgs.
"U.S. Appl. No. 14/830,255, Notice of Allowance dated Mar. 22, 2017", 9 pgs.
"U.S. Appl. No. 14/830,255, Response filed Feb. 24, 2017 to Non Final Office Action dated Nov. 25, 2016", 14 pgs.
"U.S. Appl. No. 14/830,255, Supplemental Notice of Allowability dated Jun. 13, 2017", 2 pgs.
"U.S. Appl. No. 15/623,688, Examiner Interview Summary dated Feb. 21, 2020", 2 pgs.
"U.S. Appl. No. 15/623,688, Non Final Office Action dated Aug. 8, 2019", 26 pgs.
"U.S. Appl. No. 15/623,688, Preliminary Amendment filed Jun. 15, 2017", 8 pgs.
"U.S. Appl. No. 15/623,688, Response filed Dec. 9, 2019 to Non Final Office Action dated Aug. 8, 2019", 24 pgs.
"U.S. Appl. No. 16/572,898, Preliminary Amendment filed Sep. 17, 2019", 7 pgs.
"Chinese Application Serial No. 201580002413.6, Office Action dated Sep. 28, 2017", W/English Translation, 7 pgs.
"Chinese Application Serial No. 201580039499.X, Office Action dated Jun. 27, 2019", with English translation of claims, 7 pgs.
"Chinese Application Serial No. 201580039499.X, Response filed Feb. 14, 2019 to Office Action dated Sep. 30, 2018", with English translation of claims, 20 pgs.
"Chinese Application Serial No. 201580039499.X, Response filed Sep. 10, 2019 to Office Action dated Jun. 27, 2019", with English translation of claims, 20 pgs.
"European Application Serial No. 15763675.4, Intention to Grant dated Mar. 3, 2017", 42 pgs.
"European Application Serial No. 15763675.4, Intention to Grant dated Oct. 5, 2016", 44 pgs.
"European Application Serial No. 15763675.4, Response filed Dec. 21, 2016 to Intention to Grant dated Oct. 5, 2016", 22 pgs.
"European Application Serial No. 16206030.5, Communication Pursuant to Article 94(3) EPC dated Apr. 13, 2018", 3 pgs.
"European Application Serial No. 16206030.5, Extended European Search Report dated Oct. 6, 2017", 10 pgs.
"European Application Serial No. 16206030.5, Intention to Grant dated Dec. 14, 2018", 39 pgs.
"European Application Serial No. 16206030.5, Partial European Search Report dated Jun. 2, 2017", 9 pgs.
"European Application Serial No. 16206030.5, Response filed Jul. 11, 2018 to Communication Pursuant to Article 94(3) EPC dated Apr. 13, 2018", 3 pgs.
"European Application Serial No. 16206030.5, Response filed Nov. 23, 2017 to Extended European Search Report dated Oct. 6, 2017", 6 pgs.
"European Application Serial No. 17203644.4, Extended European Search Report dated May 18, 2018", 5 pgs.
"European Application Serial No. 17203644.4, Intention to Grant dated Jan. 25, 2019", 39 pgs.
"European Application Serial No. 17203644.4, Intention to Grant dated Apr. 2, 2019", 39 pgs.
"International Application Serial No. PCT/US2015/045850m International Preliminary Report on Patentability dated Feb. 21, 2017", 6 pgs.
"International Application Serial No. PCT/US2015/045788, International Search Report dated Nov. 3, 2015", 3 pgs.
"International Application Serial No. PCT/US2015/045788, Written Opinion dated Nov. 3, 2015", 5 pgs.
"International Application Serial No. PCT/US2015/045850, International Search Report dated Nov. 4, 2015", 3 pgs.
"International Application Serial No. PCT/US2015/045850, Written Opinion dated Nov. 4, 2015", 5 pgs.
"International Application Serial No. PCT/US2015/045874, International Preliminary Report on Patentability dated Mar. 2, 2017", 8 pgs.
"International Application Serial No. PCT/US2015/045874, International Search Report dated Nov. 12, 2015", 3 pgs.
"International Application Serial No. PCT/US2015/045874, Written Opinion dated Nov. 12, 2015", 6 pgs.
"Japanese Application Serial. No. 2016-543610, Office Action dated May 18, 2017", with English translation of claims, 7 pgs.
"Japanese Application Serial No. 2017-502987, Office Action dated Nov. 21, 2017", with English translation of claims, 9 pgs.
"Japanese Office Action 2017-502987, Office Action dated Jun. 11, 2018", with English translation of claims, 6 pgs.
"Japanese Office Action 2017-502987, Response filed Apr. 20, 2018", with English translation of claims, 14 pgs.
Giuiliani, Thomas, "Reconfigurable Electrosurgical Device", Potentially related U.S. Appl. No. 14/830,069, filed Aug. 19, 2015, 34 pgs.
"U.S. Appl. No. 14/829,725, Advisory Action dated Oct. 1, 2018", 5 pgs.
"U.S. Appl. No. 14/829,725, Examiner Interview Summary dated Jun. 6, 2018", 4 pgs.
"U.S. Appl. No. 14/829,725, Examiner Interview Summary dated Jul. 23, 2018", 4 pgs.
"U.S. Appl. No. 14/829,725, Final Office Action dated Jul. 16, 2018", 34 pgs.
"U.S. Appl. No. 14/829,725, Non Final Office Action dated Mar. 9, 2018", 26 pgs.
"U.S. Appl. No. 14/829,725, Notice of Allowance dated Jul. 3, 2019", 18 pgs.
"U.S. Appl. No. 14/829,725, Response filed Jun. 5, 2018 to Non Final Office Action dated Mar. 9, 2018", 15 pgs.
"U.S. Appl. No. 14/829,725, Response filed Sep. 14, 2018 to Final Office Action dated Jul. 16, 2018", 12 pgs.
"U.S. Appl. No. 14/829,725, Supplemental Amendment filed Sep. 27, 2018", 12 pgs.
"U.S. Appl. No. 15/623,688, Final Office Action dated Mar. 19, 2020", 23 pgs.
"Chinese Application Serial No. 201810151919.9, Office Action dated May 13, 2020", w/English Translation, 15 pgs.
"International Application Serial No. PCT/US2015/045788, International Preliminary Report on Patentability dated Mar. 2, 2017", 7 pgs.
"Japanese Application Serial No. 2016-543610, Office Action dated May 23, 2017", with English Translation, 7 pgs.
"Japanese Application Serial No. 2016-543610, Response filed Aug. 23, 2017 to Office Action dated May 23, 2017", with English Translation, 13 pgs.
"Japanese Application Serial No. 2017-502987, Response filed Oct. 18, 2018 to Office Action dated Jun. 11, 2018", with English translation of claims, 8 pgs.

\* cited by examiner

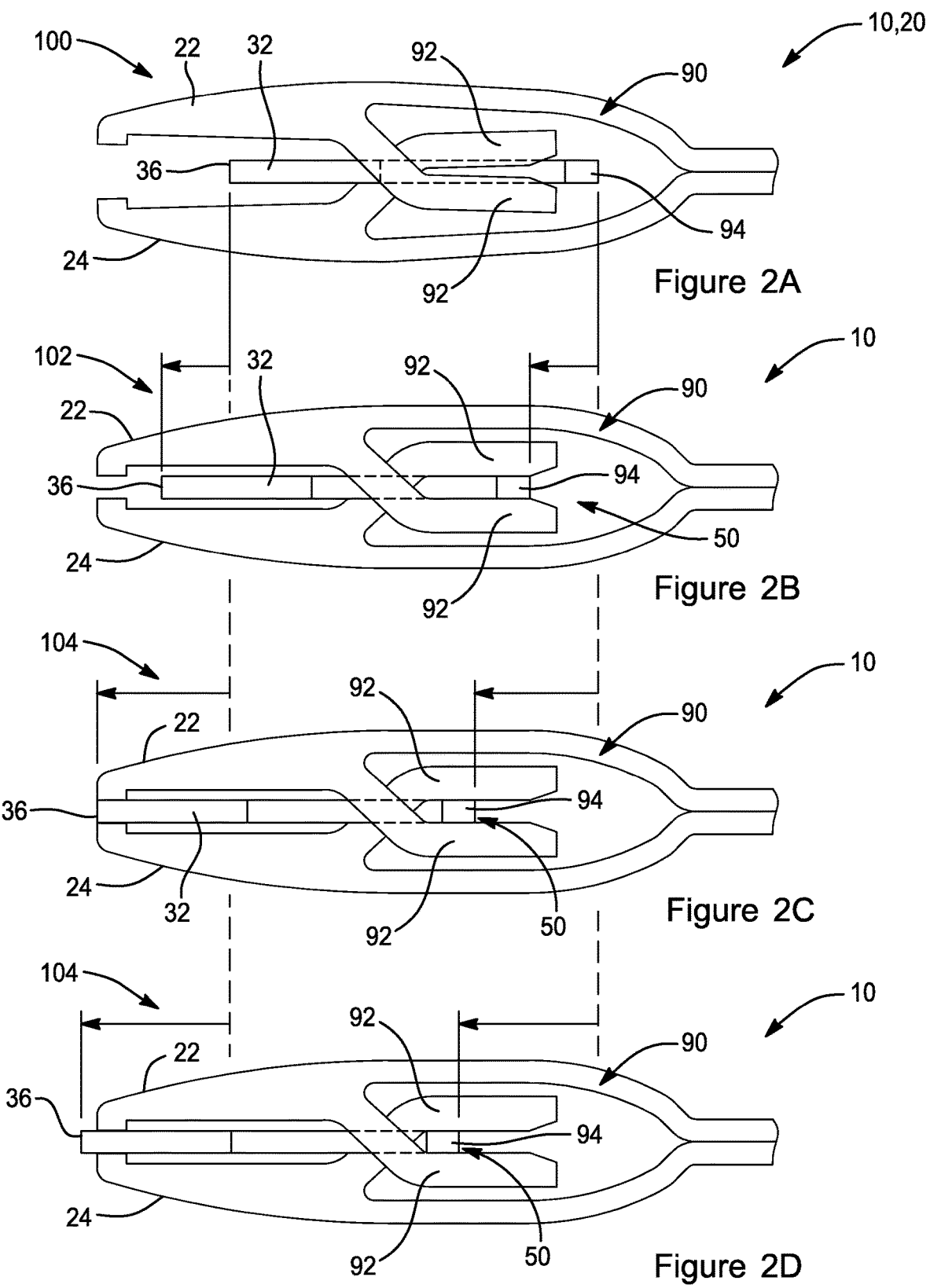

US 10,898,260 B2

RECONFIGURABLE ELECTROSURGICAL DEVICE

CROSS-REFERENCE TO RELATED APPLICATIONS

This application is a continuation of U.S. patent application Ser. No. 14/830,069, titled "Reconfigurable Electrosurgical Device," filed Aug. 19, 2015, now issued U.S. Pat. No. 10,182,861, which claims priority to U.S. Prov. Pat. Appl. No. 62/039,506, filed Aug. 20, 2014, each of which is hereby incorporated by reference herein in its entirety.

FIELD

The present teachings generally relate to an electrosurgical device that can be mechanically reconfigured into a plurality of different configurations and electrically reconfigured so that one or more different electrical configurations are available in each mechanical configuration.

BACKGROUND

Typically, electrosurgical devices have stand-alone monopolar capabilities or bipolar capabilities. Thus, a surgeon before a procedure begins may select either a device with monopolar capabilities or a device with bipolar capabilities and the surgeon can use the device to apply either monopolar power or bipolar power. For example, if the surgeon selects a monopolar device and monopolar power is not desired for the surgical procedure the surgeon may use either the device that supplies monopolar power to perform the procedure or switch to a device with bipolar capabilities. Both of these devices may be used to perform the procedure, however, switching between devices and/or using a device that may be better suited for a different purpose, may disturb the procedure flow, cause unnecessary delays in the procedure, and in some cases result in less than optimal energy sources being used.

Generally, electrosurgical devices are connected to a generator that produces a therapy signal and provides power to the electrosurgical device so that a therapy current is produced. However, the therapy currents that may be used are limited by the generator and thus if the generator is only capable of producing a single therapy current then only one therapy current can be applied through the electrosurgical device. Additionally, a generator may be capable of producing two therapy currents, but the electrosurgical device may only be capable of controlling and applying a single therapy current. Thus, the electrosurgical device may only apply a single therapy current. Some attempts have been made to produce a device that includes both monopolar capabilities and bipolar capabilities in a single device. These devices can be switched between monopolar capabilities and bipolar capabilities without switching devices. Some of these devices are reconfigurable between two mechanical configurations so that both monopolar current and bipolar current can be applied. However, the number of modes available in these devices may be restricted by the number of buttons available on the device.

Additionally, some surgical procedures require many different tools and each tool provides one or more functions that are useful during a surgical procedure. Thus, for each surgical procedure multiple different tools may be used by a surgeon to perform a surgical procedure. Changing between tools may lengthen a procedure or cause a surgeon to look away from a location and then require additional time or concentration to relocate a location of interest before continuing a procedure. Therefore, what is needed is a device that is capable of being mechanically reconfigured so that a surgeon can perform several steps with one instrument without having to change tools or field of view.

Examples of some electrosurgical instruments may be found in U.S. Pat. Nos. 6,110,171; 6,113,596; 6,190,386; 6,358,268; and 7,232,440; and U.S. Patent Application Publication Nos. 2005/0113827; 2005/0187512; 2006/0084973; 2012/0123405; 2014/0276795; and 2014/0276799 all of which are incorporated by reference herein for all purposes. It would be attractive to have an electrosurgical device that can be switched between applying a monopolar therapy current and a bipolar therapy current and three or more mechanical configurations. It would be attractive to have an electrosurgical device that may be used in open surgery as forceps and may be used for electrical cutting, hemostasis, coagulation, gripping, mechanical cutting, fulgration, or a combination thereof. What is needed is an electrosurgical device that may selectively provide two or more and preferably four or more different therapy currents in three or more configurations and preferably four or more configurations. What is needed is an electrosurgical device that produces more therapy currents than a generator supplies signals (i.e., generator modes) to the electrosurgical device. What is needed is an electrosurgical device that is electrically reconfigurable so that the electrosurgical device has fewer activation buttons then signals that the generator supplies (i.e., generator modes) yet is capable of being electrically reconfigured to apply all of the signals from the generator.

SUMMARY

The present teachings meet one or more of the present needs by providing: an electrosurgical device comprising: forceps including: (i) a first working arm and (ii) a second working arm; a blade; wherein the electrosurgical device is capable of being switched between: (A) a first mechanical configuration where the first working arm and second working arm are free to move in a direction towards each other to grasp tissue therebetween; (B) a second mechanical configuration where the first working arm and second working arm are secured together by an arm securing mechanism that prevents movement of the first working arm and the second working arm in a direction towards each other; and (C) a third mechanical configuration where the first working arm and second working arm are secured together so that the first working arm and the second working arm are prevented from moving in a direction towards each other, and the blade is substantially flush with or extend beyond a distal end of the first working arm and the second working arm; and wherein the electrosurgical device is configured to: deliver a bipolar current between the first working arm and the second working arm, and to prevent current from flowing from the blade when the electrosurgical device is in the first mechanical configuration and the second mechanical configuration; and deliver current through the blade when the electrosurgical device is in the third mechanical configuration.

The teachings herein provide: an electrosurgical device comprising: a forceps including: (i) a first working arm and (ii) a second working arm; a blade; wherein the electrosurgical device is capable of being switched between: a first mechanical configuration where the first working arm and second working arm are free to move in a direction towards each other so as to grasp tissue therebetween; a second mechanical configuration where the first working arm and second working arm are secured together to prevent movement of the first working arm and the second working arm in a direction towards or away from each other, and the blade is extended by a blade extending mechanism to be flush with the end of the working arms, and a third mechanical configuration wherein the first working arm and second working arm are secured together to prevent movement of the first working arm and the second working in a direction towards or away from each other, and the blade is extended by a blade extending mechanism to extend beyond the distal end of the working arms; wherein the electrosurgical device is configured to: deliver a bipolar current through the first working arm and the second working arm, and to prevent current from flowing from the blade when the electrosurgical device is in the first mechanical configuration; and deliver current through the blade when the electrosurgical device is in the second mechanical configuration or third mechanical configuration.

The teachings herein provide an electrosurgical device that can be switched between applying a monopolar therapy current and a bipolar therapy current and three or more mechanical configurations. The teachings herein provide an electrosurgical device that may be used in open surgery as forceps and may be used for electrical cutting, hemostasis, coagulation, gripping, mechanical cutting, fulgration, or a combination thereof. W The teachings herein provide an electrosurgical device that may selectively provide two or more and preferably four or more different therapy currents in three or more configurations and preferably four or more configurations. The teachings herein provide an electrosurgical device that produces more therapy currents than a generator supplies signals (i.e., generator modes) to the electrosurgical device. The teachings herein provide an electrosurgical device that is electrically reconfigurable so that the electrosurgical device has fewer activation buttons then signals that the generator supplies (i.e., generator modes) yet is capable of being electrically reconfigured to apply all of the signals from the generator.

BRIEF DESCRIPTION OF THE DRAWINGS

FIG. 2A illustrates an electrosurgical device that is in an unlocked state and has a retracted blade;

FIG. 2B illustrates an electrosurgical device that is in a locked state and includes a retracted blade;

FIG. 2C illustrates an electrosurgical device that is in a locked state and the blade is in a substantially flush configuration;

FIG. 2D illustrates an electrosurgical device that is in a locked state and the blade is in an extended state;

DETAILED DESCRIPTION

Figure 1A:
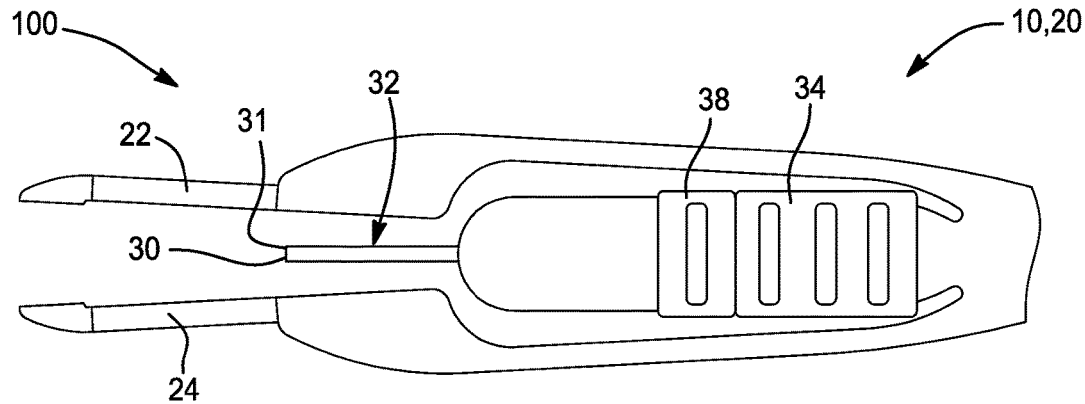
FIG. 1A illustrates an electrosurgical device in a first configuration.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 62/039,506, filed on Aug. 20, 2015, the contents of which are both incorporated by reference herein in their entirety for all reasons. The present teachings relate to an electrosurgical device. Preferably, the present teachings relate to an electrosurgical device and associated componentry that form an electrosurgical system. The electrosurgical system may be any system that includes one or more of the devices taught herein. Preferably, the electrical surgical system includes at least an electrosurgical device. The electrosurgical system may include one or more handpieces as taught herein, one or more ground pads, one or more generators, one or more electrosurgical devices, one or more adjacent handpiece components, or a combination thereof and the teachings herein of each device which are incorporated into the electrosurgical system. The electrosurgical device may be any device that may be used by a surgeon to perform a surgical procedure. The electrosurgical device may function to be switched between two or more configurations, two or more states, or both. Preferably, the electrosurgical device may be switched between three or more configurations and each configuration includes at least one mode and preferably some of the configurations include two or more modes. For example, the electrosurgical device may be switched between a monopolar configuration, a bipolar configuration, an intermediate configuration, or a combination of the three. The electrosurgical device may be any device that may be switched between two or more configurations with one hand so that a user may switch between the configurations without the need for a second hand, without disrupting the procedure, or both. The electrosurgical device may be any device and/or configuration that may be used ambidextrously, ambidextrously switched between configurations, or both. The electrosurgical device may be used to cut, perform hemostasis, coagulate, desiccate, fulgrate, electrocautery, or a combination thereof. The electrosurgical device may be any device that includes bipolar capabilities, monopolar capabilities, or both. The electrosurgical device may be used in open surgery. In addition to its electrosurgical capabilities the electrosurgical device may be used for non-electrosurgical purposes. For example, the electrosurgical device may be used as forceps, tweezers, or both that may be used to grip an object, an organ, a vein, skin, tissue, the like, or a combination thereof.

In another example, one or more parts of the device may include a sharp edge and may be used to cut, similar to that of a scalpel. The electrosurgical device may include a handpiece and a generator. The electrosurgical device may have one or more therapy signals, therapy currents, or both that extend between the handpiece and the generator.

The handpiece may be any part of the device that the user grips, that houses one or more of the control buttons, one or more switches, one or more electrical connectors, one or more diodes, one or more capacitors, or a combination thereof. The handpiece may house all or a portion of the control circuitry, a central processing unit, or both. The handpiece may electrically connect the electrosurgical device, the electrical system, or both to the generator. The handpiece may both physically connect the functional elements of the electrosurgical device and electrically connect the elements of the electrosurgical device. The handpiece may be a body portion of the electrosurgical device, a portion between the two or more working arms, may house a blade, extend and retract a blade, move working arms, be a connector between the two or more working arms, house all or a portion of the circuitry, include one or more control buttons, or a combination thereof. Preferably, the handpiece is the portion that a surgeon grips and presses one or more buttons to apply power to a desired location or applies power when an activation button, switch, foot petal, or a combination thereof is actuated. More preferably, the handpiece has a central section that includes both buttons and one or more electrical connectors for supplying power to the electrosurgical device, the working arms, the blade electrode, or a combination thereof. The handpiece may include one or more movable members, one or more handpiece components, or both. The handpiece has a proximal end (e.g., an end closest to the surgeon) and a distal end (e.g., an end farthest from a surgeon that extends into a surgical site). The tip of the handpiece is located at the distal end of the handpiece. The handpiece may allow a surgeon to supply one or more therapy signals.

The one or more therapy signals may be a signal, power, continuity, or a combination thereof. The one or more therapy signals may be an electrosurgical therapy current (hereinafter therapy current). The one or more therapy signals may extend from the handpiece to the generator or vice versa. The one or more therapy signals may be formed by the handpiece, formed by the generator, or both. The therapy signals may be a therapy current. Preferably, the therapy signals indicate that a user has performed a step and a signal is being transmitted so that therapy current, energy, or both is generated. The therapy signals may provide a signal so that one or more therapy currents are produced and the therapy currents may be used for electrosurgery. The therapy signal may be conducted when the activation circuit is in the first switch state, the second switch state, a third switch state, the handpiece is in a first position, a second position, a third position, a fourth position, or a combination of switch states and handpiece positions. The therapy signal may be conducted through the handpiece when the handpiece is in a first configuration, second configuration, third configuration, a fourth configuration, or a combination thereof. The therapy signal may be a monopolar therapy signal, a bipolar therapy signal, or both. The monopolar therapy signal may be any signal that when applied by the electrosurgical device extends from one pole of an electrosurgical device to another pole located at a remote location, off of the electrosurgical device, off the handpiece, or a combination thereof. The bipolar therapy signal may be any signal that when applied by the electrosurgical device extends from one component of a handpiece to another component of the handpiece (e.g., between two working arms, from a blade electrode to one or both working arms, or both).

The generator may be any device that supplies power, a therapy current, control signals, an electrosurgical therapy signal, or a combination thereof. The generator may function to be electrically connected to a handpiece to provide and/or receive electrosurgical therapy signals, power, therapy current, or a combination thereof. The generator may be capable of producing only a single therapy current. The generator may be capable of producing two therapy currents. The generator may include two or more power connections, three or more power connections, or four or more power connections. The power connections may be any port in the generator so that one or more power connectors of the handpiece may be plugged into so that power, control signals, therapy currents, or a combination thereof are supplied to the electrosurgical device. The generator may include one or more switches that may be switched between one or more of the power connections so that power, signals, or both may be selectively applied to the electrosurgical device based upon a desired configuration of the electrosurgical device. The generator may include a central processing unit (CPU), a series of internal switches, or both. The CPU, switches, or both may be any device that provides power, signals, electrical reconfiguration, a switch between two or more therapy currents, a switch between two or more configurations, a switch between two or more therapy signals, or a combination thereof to the electrosurgical device so that the electrosurgical device may be used to perform a desired function as is discussed herein. The CPU may be used to electrically switch the generator between a first configuration, a second configuration, a third configuration, a fourth configuration, a monopolar configuration, a bipolar configuration, a non-electrosurgical configuration, or a combination thereof in response to reconfiguration by the electrosurgical device.

The first configuration, second configuration, third configuration, and fourth configuration may be any configuration such that the electrosurgical device is mechanically reconfigured, electrically reconfigured, signally reconfigured and/or different, or a combination thereof. The first configuration, second configuration, third configuration, and fourth configuration may be any of the various configurations discussed herein. The first configuration may provide a first therapy current. Preferably, when the electrosurgical device is in the first configuration the electrosurgical device only provides the first therapy current. The first therapy current may be monopolar energy and/or monopolar current. Preferably, the first therapy current is bipolar energy and/or bipolar current. Bipolar energy may be any power source that during application extends from one pole of an electrosurgical device to another pole on the electrosurgical device. Stated another way, bipolar energy is energy that extends from one component of the handpiece to another component of the handpiece. For example, energy that extends between two working arms on the handpiece is bipolar energy, or energy that extends from a blade electrode to a working arm is a bipolar energy. The first electrical configuration may be deactivated by electrically disconnecting the one or more first activation buttons, electrically disconnecting all or a portion of an activation circuit, covering the one or more first activation buttons, electrically disconnecting the blade electrode, electrically disconnecting one or both of the working arms, shorting the blade electrode with a return pad, or a combination thereof. In the first configuration the first working arm and second working arm may be movable relative to each other (i.e., laterally movable). Preferably, the first working arm and second working arm are movable directly towards and directly away from each other within the same plane. The first working arm and second working arm may be longitudinally movable (i.e., movable along a length of the working arms). Preferably, the first working arm and the second working arm are longitudinally static and in an extended position in a first configuration. The first working arm and the second working arm may be rotationally static (i.e., may not rotate about the longitudinal axis of each respective working arm). In the first configuration the blade may be retracted. For example, the blade may be longitudinally moved towards the proximal end of the electrosurgical device so that the blade is located proximal of the working arms. The blade may be located proximal of the first working arm and second working arm. The blade may be located so that the entire length of both working arms is distal of the blade. For example, the distal end or tip of the blade may be located on the proximal side of the first working arm and the second working arm. The electrosurgical device may be mechanically reconfigured from a first configuration to a second configuration, third configuration, or fourth configuration.

The second configuration may provide any of the therapy currents discussed herein (e.g., first therapy current, second therapy current, third therapy current, or fourth therapy current). Preferably the second configuration applies the first therapy current only. The second configuration may function to be a probe and to mechanically work as a probe or provide one or more therapy currents to a location of interest (e.g., an anatomical feature). Preferably, the second configuration functions to grip a feature of interest and to lock the feature of interest between the working arms while power is applied so that a therapy current is applied to the feature of interest. More preferably, the working arms grip an anatomical feature such as a blood vessel and apply a constant amount of pressure while therapy current is applied. The amount of pressure applied may be generally the same from application to application so that the process is repeatable and provides for consistent results (e.g., cutting or coagulating). The second configuration may provide two or more different therapy currents. The second therapy current may be monopolar energy (e.g., monopolar current or monopolar power). Preferably, the second therapy current may be bipolar energy (e.g., bipolar current or bipolar power). The second electrical configuration may be deactivated by electrically disconnecting the one or more second activation buttons, electrically disconnecting all or a portion of an activation circuit, covering the one or more second activation buttons, electrically disconnecting one or both working arms, electrically disconnecting the blade electrode, shorting the first working arm with the second working arm, or a combination thereof. The second configuration may have the working arms closed and restrained and the blade electrode retracted. The working arms may be directly connected so that the working arms are prevented from, opening, closing, rotating, moving relative to each other, or a combination thereof. The working arms may include insulation therebetween and the insulation may be contacted between the first working arm and the second working arm. The first working arm and second working arm may be separated by a gap or space when the first working arm and second working arm are fully closed. A portion of a length of the first working arm and second working arm may include a gap. The gap may accommodate the blade. The gap may be present so that when an anatomical feature is gripped there between the anatomical feature is not mechanically cut and is gripped between the working arm so that the anatomical feature may be electrically cut or coagulated. The distal end, tip, or both of the blade may be located proximal of the working arms. For example, the working arms may each have a length that includes an arm portion that includes a distal end and a proximal end with the arm portion therebetween, and the blade may be located proximal of the proximal end of the working arms. The working arms in the second configuration may be restrained, prevented from moving, or both by an arm securing mechanism. The arm securing mechanism may be any device as taught herein. The blade may be moved to a retracted position by a blade extending mechanism as taught herein. The second configuration may be modified to the third configuration or the fourth configuration.

The third configuration may function to assist a surgeon in moving one or more anatomical features, provide one or more therapy currents to one or more anatomical features, or both. The third configuration may be a probe. The third configuration may function to be used as a different shaped probe than the second configuration. For example, the probe may be more blunt, have a different thickness, a different diameter, or a combination thereof than the probe in the second configuration. The third configuration may function to provide one or more different therapy currents to one or more features of interest. Preferably, the third configuration provides two or more therapy currents and more preferably four different therapy currents. The third configuration may provide a bipolar cut current, a bipolar coagulation current, a monopolar cut, a monopolar coagulation current, or a combination thereof. The third configuration may provide a therapy current from the blade to the first working arm, the second working arm, or both. The third configuration may provide a therapy current between the first working arm and the second working arm. For example, the therapy current may pass around the blade as the therapy current passes from the first working arm to the second working arm. The third configuration may provide a therapy current from the blade, the first working arm, the second working arm, or a combination thereof to a remote electrode. The third configuration may have the distal end of the blade substantially flush with or slightly proud of the distal ends of the first working arm, the second working arm, or preferably both (i.e., about 3 mm or less, about 2 mm or less, about 1 mm or less, preferably about 0.75 mm or less, and most preferably about 0 mm). Preferably, the distal ends of the blade, the first working arm, and the second working arm are all in a substantially straight line. The blade may be extended to a proximal position with the working arms by a blade extending mechanism. The blade may form a blunt tip with the working arms. The blade may create a sharp point between the working arms. The blade may be locked in position by the working arms, the arm securing mechanism, or both. The blade may be contacted on opposing sides by the working arms when the blade is a vertical configuration or a horizontal configuration so that that blade is prevented from moving relative to the working arms. The blade may include insulation on one or both sides so that the working arms do not directly contact the blade when the working arms are in contact with the blade. The blade may be electrically isolated from one or both of the working arms. The first working arm, the second working arm, or both may include insulation that electrically isolates the blade and the first working arm, the second working arm, or both. The electrosurgical device may be moved from a third configuration to a first configuration, second configuration, a fourth configuration, or a combination thereof.

The fourth configuration may function to assist a surgeon in moving one or more anatomical features, cutting one or more anatomical features, providing power to one or more anatomical features, or a combination thereof. The fourth configuration may be shaped as a blade, a probe with a blade, a probe with a blade projection, or a combination thereof. The probe may have a point where the blade extends distal of the first working arm and the second working arm. The fourth configuration may function to provide one or more different therapy currents to one or more features of interest. Preferably, the fourth configuration provides two or more therapy currents and more preferably four different therapy currents. The fourth configuration may provide a bipolar cut current, a bipolar coagulation current, a monopolar cut current, a monopolar coagulation current, or a combination thereof. The fourth configuration may provide a therapy current from the blade to the first working arm, the second working arm, or both. The fourth configuration may provide a therapy current between the first working arm and the second working arm. The fourth configuration may provide a therapy current from the blade, the first working arm, the second working arm, or a combination thereof to a remote electrode. The fourth configuration may have the distal end of the blade extending beyond the distal ends of the first working arm, the second working arm, or preferably both (i.e., about 2 mm or more, about 3 mm or more, preferably about 4 mm or more, more preferably about 5 mm or more, and most preferably about 7 mm or more). The blade may be extended to a distal position of the working arms or distally of the working arms by a blade extending mechanism. The blade may form a sharp tip beyond the working arms. The blade may be locked in position by the working arms, the arm securing mechanism, or both. The blade may be contacted on opposing sides by the working arms so that that blade is prevented from moving relative to the working arms. The blade may include insulation on one or both sides so that the working arms do not directly contact the blade when the working arms are in contact with the blade. The blade may be electrically isolated from one or both of the working arms. The first working arm, the second working arm, or both may include insulation that electrically isolate the blade and the first working arm, the second working arm, or both.

The device when in a monopolar configuration may supply power through a handpiece component (e.g., a blade electrode in a blade) and a return electrode that may be located at another location outside of the hand held portion of the electrosurgical device, through a handpiece component and an adjacent handpiece component, or both. The monopolar configuration may be any configuration where the electrosurgical device may be used to apply monopolar power. The monopolar configuration (and monopolar therapy current) is any configuration where power is supplied from a first device to a second device and the two devices are not directly connected. For example, power travels from a blade of an electrosurgical device to a ground pad and the electrosurgical device and ground pad are connected to a generator and are not directly connected. The monopolar configuration may be used to cut tissue, coagulate blood and/or fluids, electrical cutting, hemostasis, apply power to a large area, or a combination thereof. The monopolar configuration may be used to heat a specific area, heat an object between both electrodes, in contact with both electrodes, or a combination thereof. A monopolar configuration may be used so that power during use extends from a blade electrode to one or more ground pads or one or more electrodes not directly connected with the electrosurgical device so that power travels from the electrosurgical device to the remote location. The blade electrode may be used for less delicate procedures, less localized electrosurgery, or both when compared to bipolar electrosurgery.

The device when in a bipolar configuration may supply power from one portion of the device to a second portion of the device so that the return path for the power is relatively short when compared to the monopolar configuration. The bipolar configuration may be any configuration where the electrosurgical device may be used to apply bipolar power. The bipolar configuration (and bipolar therapy current) is a configuration where power travels from one electrode of a device to another electrode of the same device and the electrodes are directly connected. For example, current travels from one working arm to a second working arm and the handpiece directly electrically connects the two working arms together. The device when in the bipolar configuration may supply power between two localized handpiece components such as two working arms. The bipolar configuration may be used to coagulate, for hemostasis, cutting, fulguration, or a combination thereof. When in the bipolar configuration the electrosurgical device may include two opposing working arms. The two opposing working arms may be configured as forceps.

The forceps may function to grip, hold, squeeze, or a combination thereof one or more objects. The forceps may include one or more finger grips (i.e., configured like scissors) that may be used to move the forceps so that they may be used to grip one or more objects. The forceps may be free of finger grips and be actuated by direct pressure being applied to opposing sides of the forceps so that the forceps close and grip an object. The forceps may include a pivot point that the working arms each rotate about. The working arms may include a portion on the distal side of the pivot point and a portion on the proximal side of the pivot point. For example, the forceps may be generally "X" shaped. The working arms may extend cantilever from a central section and the working arms may each be connected to the central section. For example, the forceps may be generally "U" shaped. The forceps include at least two working arms.

The working arms (or jaws discussed herein as arms) may function to grip, hold, squeeze, or a combination thereof an object when the object is between the two or more opposing working arms. The working arms may include one or more gripping features that may assist in gripping, holding, squeezing, or a combination thereof an object. Each of the working arms include an electrode so that power can pass through each of the working arms. The first working arm includes a first electrode and the second working arm includes a second electrode. The working arms may be movable between two or more positions. Preferably, the working arms are movable between at least a first position and a second position. For example, the working arms may be movable between a bipolar configuration (e.g., first position) and a monopolar configuration (e.g., second position). The working arms in the first position may be off, energized, one working arm may be energized, or a combination thereof. The working arms in the second position may be off, one or both of the working arms may be electrically disconnected, one or both of the working arms may be electrically connected, one working arm may be shorted by the other working arm, or a combination thereof. More preferably, in the second position the working arms are immobilized so that the working arms cannot be used as forceps. For example, the working arms may be connected together by a securing mechanism or an arm securing mechanism. The working arms may be flexible so that the working arms when moved towards each other flex to create the movement and gripping force. The working arms may bend, deform, elastically deform, or a combination thereof. The working arms may be bias open (i.e., the neutral position for the working arms may be in the open state where the arms are separate). The working arms may be bias closed (i.e., the neutral position for the working arms may be in the closed state where the arms are together). The working arms may be longitudinally static and moveable relative to each other. The working arms may be longitudinally moveable and may be moveable relative to each other (i.e., laterally movable) so that a gripping force or an opening force may be created. The working arms may be rotatable about a longitudinal axis, an axis of the working arms, or both. Preferably, the working arms are rotationally static and cannot be rotated. The working arms may be retractable and/or extendable individually, simultaneously, or both. The working arms may be selectively retractable and/or extendable so that one or more tip regions of the working arms, the blade, or both are exposed.

The working arms include a tip region. The tip region may include a portion that is configured to assist in facilitating gripping, holding, squeezing, or a combination thereof. Additionally, the tip region may be configured in one or more electrosurgical configurations (e.g., a monopolar configuration, bipolar configuration, or a combination of both). The tip region may include teeth, serrations, mouse teeth, be free of teeth (i.e., smooth), or a combination thereof. The tip region may be fully and/or partially insulated. Preferably, the tip region includes insulation on the non-contact portions of the working arms so that electrosurgical energy is not transferred through incidental contact. The tip region may include one or more electrodes that supply power through the working arms to a location of interest. The working arms may include an active portion (i.e., an electrode) and an inactive portion (i.e., an insulated portion).

The active portion may function to apply power. The active portion may be the same portion as the contact regions of the forceps. Thus, for example, when tissue is grasped between the contact portions of the forceps, power may be supplied to the tissue through this contact portion. The active portion of the working arms preferably is between the two opposing working arms or on a distal end of each working arm and the active portion of the blade electrode is the portion that extends beyond the working arms, or a distal end of the blade. The active portions may be substantially surrounded by inactive portions or portions that are insulated. The inactive portion may be any portion that does not supply power, that is insulated, or both. The active portion may be any portion that may transfer power through incidental contact and thus are insulated so that incidental transfer of power does not occur and/or stray current is prevented. For example, an outside of the working arms may be coated with an insulating material so that if the working arms accidentally contact tissue proximate to the tissue of interest the proximate tissue is not subjected to a transfer of power. The inactive portion and the active portion may be made of different materials, coated with different materials, or both. The active portion of the working arms, the blade, or both may provide a therapy signal to a remote electrode.

The remote electrode may function to complete a circuit. The remote electrode may function to complete a monopolar circuit. The remote electrode may be indirectly connected to the electrosurgical device. The remote electrode may be connected to the electrosurgical device through the generator. The remote electrode may be located a distance away from the electrosurgical device. The remote electrode may be a ground pad, a return pad, or both. The remote electrode may only receive a therapy current when monopolar power is supplied through the electrosurgical device. The remote electrode may not be part of the electrosurgical device, but may be in electrical communication with the blade, the one or more working arms, or both in the first configuration, second configuration, third configuration, fourth configuration, or a combination thereof. The one or more working arms may be connected together by one or more securing mechanisms, arm securing mechanisms, an electromagnetic latching system, or a combination thereof.

The electromagnetic latching system may function to lock two working arms together, assist in creating a gripping force, assist in moving the working arms apart, or a combination thereof. The electromagnetic latching system may be used with a securing mechanism, an arm securing mechanism, or both. Preferably, the electromagnetic latching system is used instead of the securing mechanism and the arm securing mechanism. The electromagnetic latching system may magnetically move the working arms relative to each other. The electromagnetic latching system may magnetically lock the working arms in any of the configurations discussed herein. The electromagnetic latching system may include one or more electromagnetic latches.

The one or more electromagnetic latches may function to lock the working arms together, assist in moving the working arms towards and/or away from each other, maintaining the working arms in one of the configurations taught herein. The one or more electromagnetic latches may move the working arms together when a first polarity is applied and apart when an opposite polarity is applied. The one or more electromagnetic latches may be attracted to an opposing electromagnetic latch, a magnetic material, metal, or a combination thereof. The one or more electromagnetic latches may be turned on and off. The electromagnetic latches may be located in a distal end region (i.e., a rear half of the device). The electromagnetic latches may be located in a proximal end region (i.e., a front half of the device). The electromagnetic latches may be connected to or part of an immobilization arm. The electromagnetic latch of a first working arm may be free of contact with an electromagnetic latch of a second working arm. Preferably, the first working arm includes a first electromagnetic latch and the second working arm includes a second electromagnetic latch. Each working arm may include two or more electromagnetic latches so that the amount of force generated may be varied. The electromagnetic latches may elastically deform the working arms to create a gripping force. The electromagnetic latches may move the working arms about a movable connection.

The movable connection may function to allow a hinging action, movement back and forth (i.e., lateral direction), or both. The movable connection may create a force (e.g., a biasing force) that opposes a gripping of the forceps so that the forceps default open or to a neutral position; is in the direction of gripping so that the forceps default closed or to a neutral position; or a combination of both. The neutral position may be where the working arms are spread apart with a gap between the working arms or the arms are closed. The movable connection may create the resilient moving forces. The movable connection may be free of generating forces or storing energy. For example, the movable connection may allow for movement of components and a biasing device may move the components. The movable connection may create a pivot point that opposes a rigid connection or a rigid portion (e.g., central section). The movable connection may include a pin that one or both of the working arms rotate or move about. The movable connection may be free of a pin. The movable connection may be a location of deflection such as a deflecting beam or a cantilever segment that deflects. The rigid section may remain static while the movable section moves about the rigid section. The rigid section may form a side of the movable connection that anchors the movable section so that the movable section may move, flex, pivot, or a combination thereof. The movable section may be any shape so that the movable section moves. The pivot point may function to allow the working arms to move relative to each other (i.e., laterally). The pivot point may separate the electrosurgical device into two halves. The pivot point may allow the working arms to move toward and away from each other. The pivot point may rotationally move the working arms. The pivot point may allow the securing mechanism, the electromagnetic latching system, or both to lock the working arms together. The pivot point may be located between the working arms and the immobilization arms. The pivot point may be a point where the working arms connect to a central section and the working arms flex about so that the working arms move towards each other. The movable section may be restrained my one or more securing mechanism, one or more electromagnetic latching systems, or both.

The securing mechanism, arm securing mechanism, or both may function to lock the first working arm to the second working arm so that the first working arm and the second working arm are not movable relative to each other. The securing mechanism may be laterally movable with the working arms and may form a connection any time the working arms are pressed together. The securing mechanism may mechanically and directly connect the first working arm to the second working arm. For example, a device may extend between the first working arm and the second working arm and prevent the working arms from moving relative to each other. The securing mechanism may include features on the first working arm, the second working arm, or both the first working arm and the second working arm. The securing mechanism may include one or more devices that extend from the first working arm to the second working arm. The one or more devices may be a resilient tongue that extends from the first working arm to the second working arm.

The resilient tongue may function to extend between and connect the first working arm and the second working arm together. The resilient tongue may prevent movement of the first working arm relative to the second working arm. The resilient tongue may only be extendable when the blade is retracted. The resilient tongue may flex and extend through a slot in the opposing arm to form the connection. The resilient tongue may partially extend through a slot in an opposing working arm. The resilient tongue may have another tongue that extends from a main portion of the resilient tongue and the tongue may form a connection with a latch and this connection may prevent movement of the working arms relative to each other.

The tongue may function to connect or lock the first working arm with the second working arm. The resilient tongue may include one or more tongues. The resilient slider may include a plurality of tongues so that the working arms may be locked in different positions so that the locked position between the first working arm and the second working arm is selectable. The plurality of tongues may allow for the working arms to be selectively positioned relative to each other or the force between the working arms to be selectively chosen. The tongue may form a connection with a slot, a latch slider, an edge of a latch slider, or both. The tongue may project substantially perpendicular to the resilient tongue and form a catch. The tongue may have an angled portion and a flat portion. The angled portion may allow for one way movement. The flat portion may prevent movement of the tongue in a direction. The tongue may extend through a slot in an opposing arm.

The slot may function to permit all or a portion of the resilient tongue to extend therethrough to create a locked relationship. The slot may be on an edge and of the working arm. The slot may be square, rectangular, circular, oval, symmetrical, non-symmetrical, or a combination thereof. The slot may allow for a tongue to catch a wall of the slot to prevent movement of the working arms. The slot may receive a latch slider and permit the latch slider to prevent movement of the working arms, while a portion of the resilient tongue extends through the slot.

The latch slider may function to restrict movement of the first working arm and the second working arm together. The latch slider may contact a portion of the tongue, resilient tongue, or both and prevent movement of the working arms relative to each other. The latch slider may move between one or more tongues so that the tongues provide selective locking between the first working arm and the second working arm. The latch slider may laterally move, longitudinally move, rotationally move, or a combination thereof to permit the working arms to be selectively locked, released, or both. The latch slider may contact an edge of the tongue and prevent the tongue and working arms from moving away from each other. The latch slider may assist in the securing mechanism being a selectable mechanical latch. The latch slider and securing mechanism may be used in lieu of or in addition to an arm securing mechanism. However, the electrosurgical device may be free of any securing mechanisms and may include only arm securing mechanism.

The one or more arm securing mechanisms may function to lock the working arm relative to each other. The arm securing mechanisms may prevent a first working arm from moving relative to a second working arm. The arm securing mechanisms may lock the working arms together. The arm securing mechanism may move the first working arm and the second working arm into contact. The arm securing mechanism may lock the blade in a proximal portion, in a flush position, in an extended position, between the working arms, or a combination thereof. The arm securing mechanism may secure the arms in an open state, a closed state, or both. The arm securing mechanism may prevent advancement of the blade without locking the working arm together. The arm securing mechanism may allow for some elastic movement of the arms so that the blade may be longitudinally movement between the arms while the arms are in a locked state. The arm securing mechanisms may include one or more immobilization arms, one or more immobilization members, or both The one or more immobilization arms, one or more immobilization features, or both may be any feature of the housing, the working arms, or both that may immobilize one or both working arms when the electrosurgical device is in the monopolar configuration, second configuration, third configuration, fourth configuration, or a combination thereof. The immobilization arms may be connected to the working arms and extend between one or both of the working arms and when the blade electrode is advanced the immobilization arms are separated and the working arms are moved into contact with each other. The immobilization arms may permit some elastic deformation of the working arms so that the blade may be longitudinally moved between the working arms as the electrosurgical device is changed between the second configuration, third configuration, and fourth configuration. The immobilization arms may be connected to the working arms and extend between one or both of the working arms and when the blade, the immobilization member, or both is advanced the immobilization arms are compressed, pushed together, or both and the working arms are moved into contact with each other. The immobilization arms may be generally parallel to the working arms, may extend: in the same direction as the working arms, may extend away from the working arms, towards an opposing working arm, towards the user, away from a user, or a combination thereof. Preferably, the working arms and the immobilization arms form generally an "X" shape so that when one side of the "X" is moved outward the opposing side of the "X" is moved inward. For example, as the blade, immobilization member, or both is moved forward the blade electrode may include a wedge and the wedge may act to force the immobilizing arms apart so that the working arms are moved together. The working arm and the immobilization arms may form generally two "V" shapes. The two generally "V" shapes may extend generally in the same direction so that as one V is widened the other V is narrowed. The immobilization arms may overlap. The overlap portion may form the "V" shape. For example, one immobilization arm may extend from the housing, a first working arm, or both towards the second working arm, the housing proximate the second working arm, or both, and a second immobilization arm may extend from the housing, a second working arm, or both towards the first working arm and as an immobilization feature such as a wedge is moved between the first immobilization arm and the second immobilization arm the immobilization arms may be moved closer to the opposing working arm so that the working arms are moved into contact and immobilized. The housing, the working arms, or both may be free of immobilization arms.

The two or more working arms may be immobilized by an immobilization member. The immobilization member may be any feature that connects the two or more working arms together so that the arms are immobilized in the monopolar configuration, so that the forceps are disabled, or both. The immobilization members may be part of the arms, part of the housing, all or a part of the shuttle, or a combination thereof. The immobilization members may be a track that extends along all or a portion of each arm and as the shuttle is moved forward or backward to the monopolar configuration, each track may extend into communication with the shuttle so that each of the working arms are moved into contact with each other and vice versa from the bipolar configuration. The immobilization member may be a lock, a fastener, a piece that houses all or a portion of the working arms, or a combination thereof that locks the two working arms together. The immobilization member may be a piece that slides and compresses the working arms, a piece that twists and radially compresses the working arms, or a combination of both. The immobilization member may be a wedge, a ring, or both. The immobilization member may be wedge shaped that the wedge when moved assists in moving one or more immobilizing arms without having a step of separating the immobilizing arms. The wedge may have a tapered shape with a point on one end so that the wedge fits between the two opposing immobilization arms and as the wedge is gradually progressed between the immobilizing arms the wedge becomes wider moving the immobilizing arms apart. The wedge may be generally triangular in shape. The wedge may have a shape that is a mirror image to the shape formed between the immobilization arms so that when the tip of the wedge reaches the pointed portion between the immobilization arms the wedge is prevented from moving further forward. The wedge may be located at any location on the electrosurgical device, the shuttle, or both so that when the wedge is moved between the immobilization arms the wedge immobilizes the working arms. The immobilization member may be ring shaped. The ring shaped immobilization members may be any device that assists in immobilizing the working arms. The ring may extend around all or a portion of the periphery, a perimeter, or both of the electrosurgical device, the working arms, the immobilization arms, or a combination thereof. The ring may move along the outside of the electrosurgical device so a portion of the electrosurgical device is located within an inner portion of the ring. The ring may be a complete circle, a partial circle, "U" shaped, fully surround a length of the device, partially surround a length of the device, or a combination thereof. The ring may be part of the shuttle, may be the shuttle, may be discrete from the shuttle, may assist in moving the blade electrode, may cover one or more of the activation buttons, may extend under the one or more activation buttons, may extend through one or more activation buttons, deactivate all or a portion of an activation circuit, may fully and/or partially surround one or more of the immobilization arms, or a combination thereof. The immobilization member while being moved and immobilizing may move a blade, may extend a blade, or a combination of both. Preferably, the immobilization member both restricts movement of the immobilization arms and longitudinally moves the blade so between the configurations taught herein.

The blade may function to cut, supply a monopolar therapy current, provide a sharp point, provide a blade edge, or a combination thereof. The blade may be any device that may be used to apply monopolar power during a procedure, that may be longitudinally movable, rotationally movable, extendable, retractable, or a combination thereof. The blade may be static. Preferably, in one embodiment the blade may be static and the working arms moved relative to the blade so that when the working arms are moved the blade is exposed. More preferably, the blade is a movable. The blade includes a distal end. The distal end is located on the opposite end of the electrosurgical device as the user, a gripping region, or both. The blade may have a first position (e.g., retracted), a second position (e.g., partially extended), a third position (e.g., substantially flush), and a fourth position (e.g., extended, or fully extended).

The first position may function to permit the working arms to move relative to each other without the blade interfering with movement of the working arms. The first position may function to allow for a therapy current to pass between working arms without interference from the blade. The first position may be where the blade is located relative to the working arms so that the working arms are past the blade (e.g., the blade is retracted so that the working arms extend past the blade or the working arms are extended so that the working arms extend past the blade). In the first position, the distal end of the blade may be located proximal of the entire length of the working arms. The first position may be where the blade is electrically disconnected, electrically shorted relative to another handpiece component, electrically insulated so that power cannot pass from the blade, or a combination thereof. The first position may be where the blade is substantially located within the handpiece, no part of the blade extends between the working arms, or both. The first position may be different from second position, third position, fourth position, etc. . . .

The second position functions permit the working arms to be located together in direct contact without interference from the blade. The second position functions to partially extend a blade so that a gap is present between the first working arm and the second working arm. The blade in the second position may be in the same location as the blade in the first position and only the working arms may change position. The second position may be where the distal end is located on a proximal side of the distal end of the first working arm, the second working arm, or both. The second position may provide two or more therapy currents. The second position may apply only a bipolar therapy current. The second position may apply a therapy current from the working arms, from the blade through the working arms, from the blade between the working arms, or a combination thereof. The second position may have a position that is proximal to that of a third position.

The third position may function to create a space between the first working arm and the second working arm. The third position may function to permit therapy currents to flow between the first working arm and second working arm without interference from the blade. The third position may allow for power to flow from the blade electrode. The electrosurgical device may be used as a probe in the third position. The third position may function to allow a therapy current to pass from the blade to one or both working arms or vice versa. The third position may have the blade extended so that the blade is substantially proud, substantially flush, or both with one or both working arms. The third position may have the distal ends of the blade, the first working arm, and the second working arm all substantially aligned. The third position may have the blade locked between the first working arm and the second working arm. The third position may be located distal of the second position and proximal of the fourth position.

The fourth position may function to create a cutting surface, a cutting edge, or both. The fourth position may function to extend the blade between the working arms to disrupt therapy current from passing from the first working arm to the second working arm. The blade in the fourth position may be fully extended. The blade in the fourth position may be locked between the first working arm and the second working arm. The blade may be advanced or retracted by a blade extending mechanism.

The blade extending mechanism may function to move the blade between the first position, second position, third position, fourth position, or a combination thereof. The blade extending mechanism may be directly connected to the blade, indirectly connected to the blade, or both. The blade extending mechanism may be a first slider, a second slider, a shuttle, an immobilization member, or a combination thereof. The blade extending mechanism may have one or more detent positions so that a user can lock the blade in each of the positions discussed herein. The blade extending mechanism may lock the blade in each of the positions and then unlock the blade to permit the blade to be moved. The blade extending mechanism may move (i.e., in a proximal direction or a distal direction) along the longitudinal axis of the electrosurgical device, the working arms, or both. The blade extending mechanism may move with the assistance of one or more biasing devices.

The bias device may be any device that may act to retract and/or advance one or more components of the electrosurgical device. The bias device may act to separate the working arms of the electrosurgical device when in the bipolar configuration. The bias device may push the blade and/or shuttle between one or more of the configurations, pull the blade and/or shuttle back from the one or more configurations, or a combination thereof. The bias device may ensure that the shuttle, first slider, second slider, blade, working arms, monopolar electrode, blade, or a combination thereof are in a fully extended position, substantially flush position, partially extended position, fully retracted position, or a combination thereof. For example, if a user moves a shuttle or slider towards a forward position and stops short, the bias device may complete the movement to a final position. The bias device may assist in moving any of the devices and/or features discussed herein so that the devices and/or features are bi-stable, tri-stable, or quad-stable. For example, the bias device may ensure that the blade electrode is always either fully extended or fully retracted and not located therebetween. The bias device may be a spring, a piece of rubber, an elastomeric piece, a bend in metal that forms a bias surface, a detent or a combination thereof. If the bias device is bent metal the metal may be bent forming more than one plane. The first plane may contact a first surface and the second arm may contact a second surface so that two opposing electrosurgical components are moved. The bias device may be connected to the blade, a shuttle, first slider, second slider, between the working arms, or a combination thereof.

The shuttle may function to cover one or more activation buttons, moves the blade, moves one or both working arms, immobilizes and/or electrically disconnects one or more features of the electrosurgical device, immobilizes one or more activation buttons, impedes movement and/or depression of one or more activation buttons, move one or more immobilization arms, moves one or more sliders, moves a plurality of sliders simultaneously, or a combination thereof. The shuttle may be a solid piece. The shuttle may include one or more positions and preferably a plurality of positions. Preferably, the shuttle includes at least a first position, a second position, a third position, a fourth position, or a combination thereof. The shuttle may be moved by sliding on a track. The shuttle may be a slider assembly that moves the blade. The shuttle may be movably connected to one or more sliders. The shuttle may connect a first slider and a second slider together. The shuttle may be snapped over a plurality of sliders. The shuttle may laterally connect a plurality of sliders together. The shuttle may be a discrete piece that may connect two or more sliders together. For example, the shuttle may move multiple sliders so that the working arms are locked together and the blade may be extended or the working arms are released and the blade is retracted. In another example, the shuttle may lock the blade electrode in a forward position and immobilize both of the working arms when the electrosurgical device is configured for monopolar use. The shuttle may lock by a detent, a projection that locks in a corresponding recess, a mechanical interlock, a friction fit, a mechanical lock, or a combination thereof. This shuttle may be connected to one or both working arms of the electrosurgical device. The shuttle may be directly connected to the immobilization member.

The first slider, the second slider, or both function to move one or more elements of the electrosurgical device to lock the electrosurgical device, reconfigure the electrosurgical device, unlock the electrosurgical device, prevent actuation of one or more activation buttons, or a combination thereof. The first slider, the second slider, or both may move longitudinally along the electrosurgical device. The first slider may prevent movement of the second slider in some configurations or vice versa. The electrosurgical device may only include one slider. The slider when moved may lock and unlock the working arms and extend and retract the blade. The slider may only lock and unlock the working arms or extend and retract the blade. For example, the first slider may lock and unlock the working arms and the second slider may extend and retract the blade or vice versa. The first slider, the second slider, or both may include an immobilization member, may actuate an electromagnetic latching system, or both. The first slider the second slider or both may be connected together by a shuttle that moves both of the working arms together. The first slider, the second slider, or both may cover and uncover activation buttons as the first slider and second slider are moved between the various configurations taught herein so that different electrical modes or electrical functions may be applied (e.g., monopolar cut, monopolar coagulation, bipolar cut, bipolar coagulation).

FIG. 1A is a top view of an electrosurgical device 10 that as shown is configured as forceps 20. The forceps 20 include a first working arm (or jaw) 22 and a second working arm (or jaw) 24. The electrosurgical device 10 is shown in a first configuration 100 where the first working arm 22 and the second working arm 24 are movable relative to each other. The blade 32 includes a tip 31 with a blade electrode 30 within the tip 31. The blade 32 is located between the first working arm 22 and the second working arm 24. The electrosurgical device 10 includes a first slider 34 and a second slider 38 that is located adjacent to the first slider 34 in a proximal position (e.g., first position). As shown, the first slider 34 and the second slider 38 are located in a proximal position so that the second slider 38 locks the first slider 34 in place.

Figure 1B:
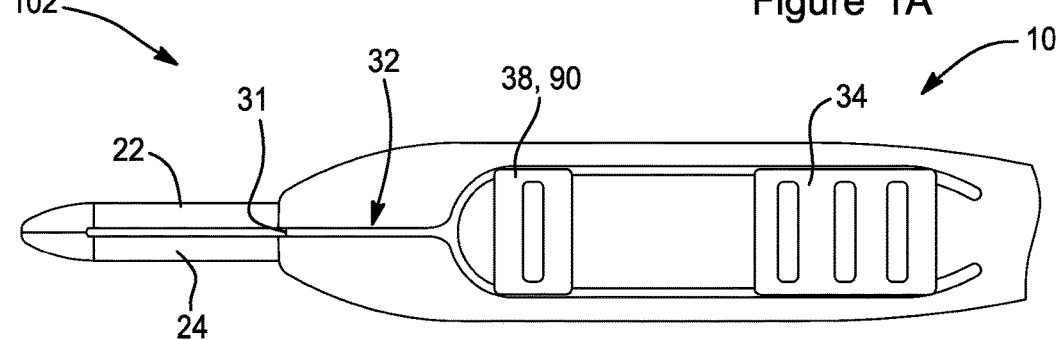
FIG. 1B illustrates the electrosurgical device of FIG. 1A in a second configuration.

FIG. 1B is a top view of an electrosurgical device 10. The electrosurgical device 10 is shown in a second configuration 102 where the first working arm 22 and the second working arm 24 are in direct contact and in a locked position. A blade 32 is located within the electrosurgical device 10 with the tip 31 located proximal of the first working arm 22 and the second working arm 24 so that the blade 32, as shown, is not located between the working arms. The second slider 38 is shown in a second position where the first slider 34 is not restricted by the second slider 38. The second slider 38 acts as an arm securing mechanism 90 that restricts movement of the first working arm 22 and the second working arm 24 relative to each other. The first slider 34 is located in a proximal position (e.g., first position) and retains the blade 32 between proximal ends of the working arms 22, 24.

Figure 1C:
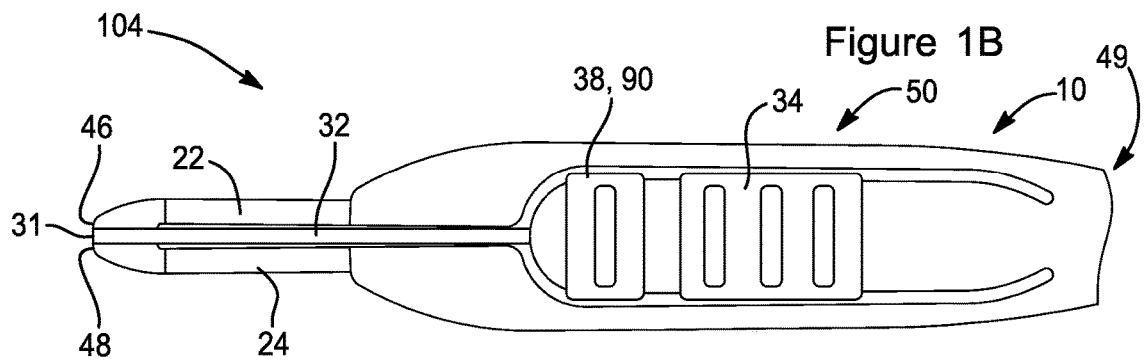
FIG. 1C illustrates the electrosurgical device of FIG. 1A in a third configuration.

FIG. 1C is a top view of an electrosurgical device 10. The electrosurgical device 10 is shown in a third configuration 104 where the first working arm 22 and the second working arm 24 are in a locked position with the blade 32 extending therebetween so that the first working arm 22 contacts the blade 32 on a first side and the second working arm contacts the blade 30 on a second side. The blade 32 is extended between the first working arm 22 and the second working arm 24 by the blade extending mechanism 50, which is also the first slider 34 so that the tip 31 is substantially flush with the distal end 46 of the first working arm 22 and the distal end 48 of the second working arm 24. The distal ends 46, 48 are located on an opposite end of the electrosurgical device as the proximal end 49, which is located closest to a user. The second slider 38 is in the second position and the first slider 34 is moved into an intermediate position (e.g., second position) where the first slider 34 advances the blade 32 so that the tip 31 is flush with the distal end 46 of the first working arm 22 and the distal end 48 of the second working arm 24. The second slider 38 is an arm securing mechanism 90 that restricts movement of the first working arm 22 and the second working arm 24 while the blade is extended 32.

Figure 1D:
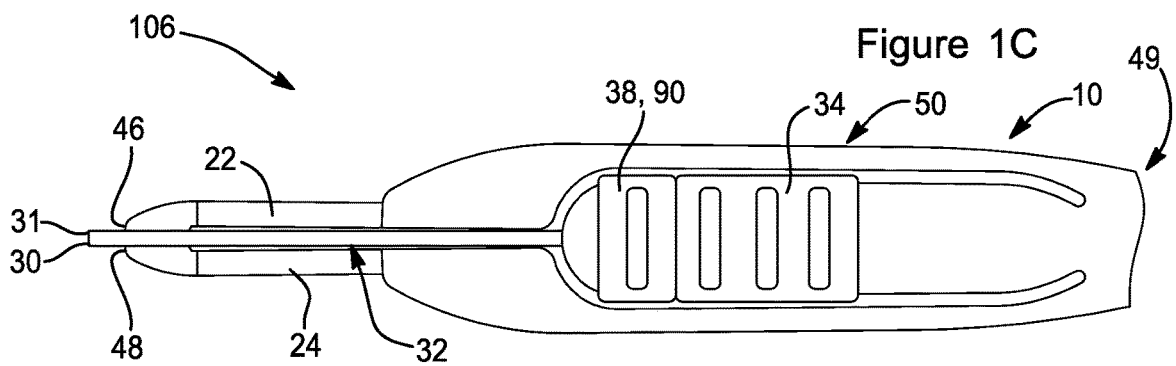
FIG. 1D illustrates the electrosurgical device of FIG. 1A in a fourth configuration.

FIG. 1D illustrates a top view of the electrosurgical device 10 in a fourth configuration 106. In the fourth configuration 106, the blade 32 is extended by the blade extending mechanism 50 so that the tip 31 including the blade electrode 20 extends beyond the distal end 46 of the first working arm 22 and the distal end 48 of the second working arm 24. The distal ends 46, 48 are located on an opposite end of the electrosurgical device as the proximal end 49, which is located closest to a user. The second slider 38 is in the second position and the second slider 38 is locked in position by the first slider 34 that is moved into the distal position (e.g., third position). The first slider 34 as it is advanced from the intermediate position to the distal position advances the blade 32 where the tip 31 extend beyond the working arms 22, 24. The second slider 38 is an arm securing mechanism 90 that restricts movement of the first working arm 22 and the second working arm 24 while the blade is extended 32.

FIG. 2A illustrates an electrosurgical device 10 in a first configuration 100 as forceps 20. The electrosurgical device 10 includes a first working arm 22 that is opposing a second working arm 24 with a blade 32 there between. The blade 32 is in a retracted state where the distal end 36 of the blade 30 is located proximal of the working arms 22, 24. The electrosurgical device 10 includes an arm securing mechanism 90. The arm securing mechanism 90 includes a pair of opposing immobilization arms 92. The immobilization arms 92 are located opposite the working arms 22, 24 and extend in an opposite direction. An immobilization member 94 is located in a first position that is proximal of the ends of the immobilization arms 92 and in line with a gap between the immobilization arms 92 and the arms are free to move along the lateral direction.

FIG. 2B illustrates a second configuration 102 of the electrosurgical device 10 where the immobilization member 94 of the arm securing mechanism 90 is moved forward, the distance indicated, to a second position between the immobilization arms 92. The immobilization device locks the immobilization arms 92 apart and advances the blade 30 an equal distance forward between the first working arm 22 and the second working arm 24 as the arm securing mechanism 90 moves. The distal end 36 of the blade 32 is moved towards the distal ends of the working arms 22, 24 by the immobilization member which is also a blade extending mechanism 50, but the blade 32 is still located inside of the ends of the working arms 22, 24.

FIG. 2C illustrates a third configuration 104 of the electrosurgical device 10 where the immobilization member 94 of the arm securing mechanism 90 is advanced forward to a third position between the immobilization arms 92. In advancing the arm securing mechanism 90 to the third position the immobilization arms 92 and working arms 22, 24 remain locked and the tip 36 of the blade 32 is moved, by the blade extending mechanism 50, to be flush with the distal ends of the first working arm 22 and the second working arm 24.

FIG. 2D illustrates a fourth configuration 106 of the electrosurgical device 10 where the immobilization member 94 of the arm securing mechanism 90 is advanced to a fourth position between the immobilization arms 92 where the immobilization member 94 is prevented from further advancing. In advancing the immobilization member 94, which is also the blade extending mechanism 50, the blade 32 is also advanced so that the tip 36 of the blade 32 extends beyond the distal ends of the first working arm 22 and the second working arm 24. FIG. 2D illustrates the distance the blade 32 and immobilization member 94 are moved relative to the first configuration 100, second configuration 102, and third configuration 104.

Figure 3:
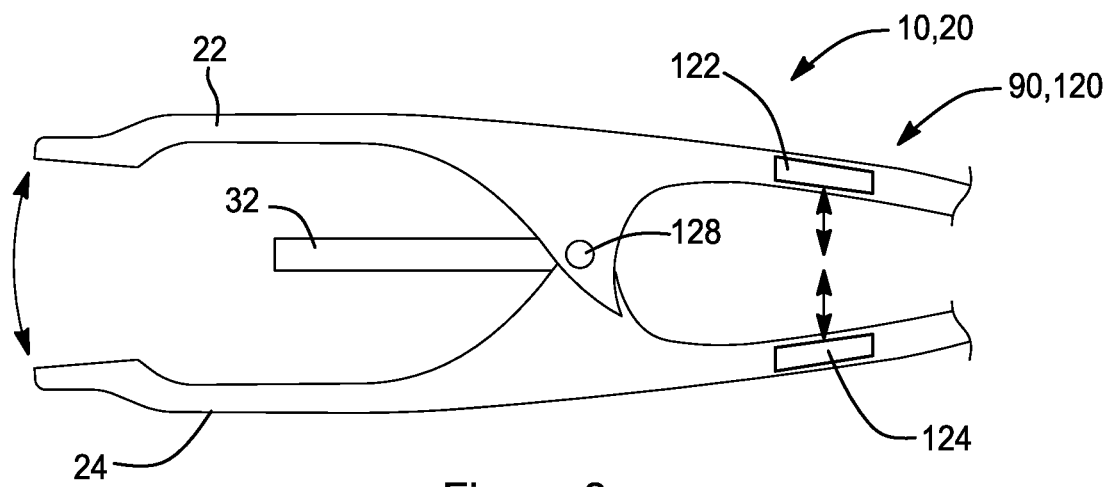
FIG. 3 illustrates an electrosurgical device including an electromagnetic latching system on a rear half that locks and unlocks the electrosurgical device.

FIG. 3 illustrates an electrosurgical device 10 that includes arm securing mechanism 90, which is an electromagnetic latching system 120. The electrosurgical device 10 is configured as forceps 20 with a first working arm 22 and a second working arm 24 with a blade 32 therebetween. A pivot point 128 connects the first working arm 22 and the second working arm 24 so that the working arms are movable relative to each other to create a gripping force. As shown a first electromagnetic latch 122 and a second electromagnetic latch 124 are located on the proximal side of the pivot point 128. The proximal side of the pivot point 128 may be an extension of the working arms 22, 24 or may be immobilization arms 92. As shown, the proximal side of the pivot point 128 is an extension of the working arms 22, 24. When the electromagnetic latching system 120 is activated the first electromagnetic latch 122 is moved away from the second electromagnetic latch 124 to create a gripping force, or the electromagnetic latching system 120 is reverse activated so that the first electromagnetic latch 122 is attracted towards the second electromagnetic latch 124 opening the forceps and releasing a gripping force.

Figure 4:
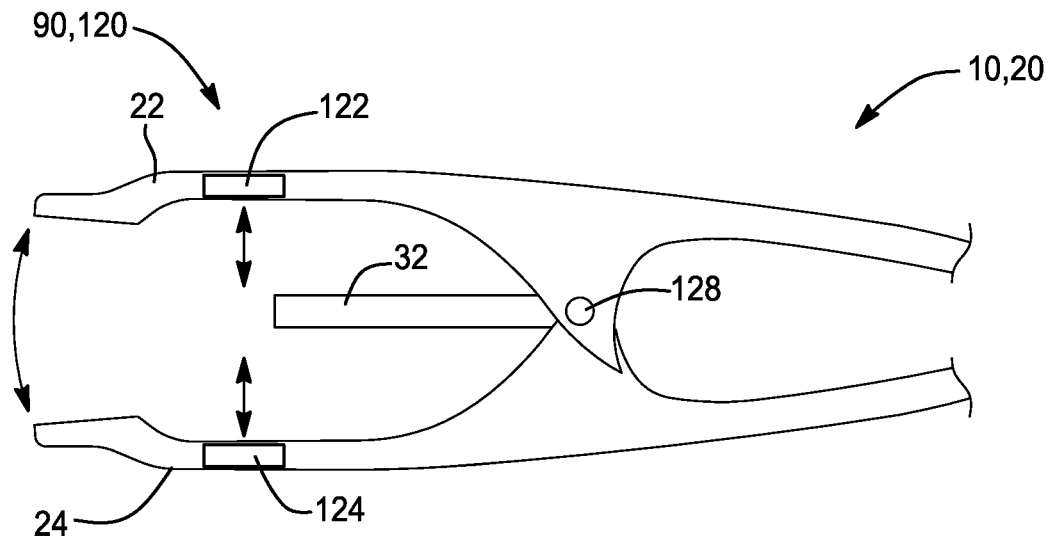
FIG. 4 illustrates an electrosurgical device including an electromagnetic latching system on a front half that locks and unlocks the electrosurgical device.

FIG. 4 illustrates an electrosurgical device 10 that includes an immobilization device 90, which is an electromagnetic latching system 120. The electrosurgical device 10 is configured as forceps 20 with a first working arm 22 and a second working arm 24 with a blade 32 therebetween. As shown a pivot point 128 connects the first working arm 22 and the second working arm 24 so that the working arms are movable relative to each other to create a gripping force, although the working arms 22, 24 could extend cantilever from a central portion or body portion as is shown above in FIGS. 1A-1D. The working arms 22, 24 include a first electromagnetic latch 122 in a first working arm 22 and a second electromagnetic latch 124 in a second working arm 24 with a blade 32 located between the first working arm 22 and the second working arm 24. When the electromagnetic latching system 120 is activated the first electromagnetic latch 122 is moved towards the second electromagnetic latch 124 to create a gripping force, or the electromagnetic latching system 120 is reverse activated so that the first electromagnetic latch 122 is repelled from the second electromagnetic latch 124 opening the forceps and releasing a gripping force.

Figure 5:
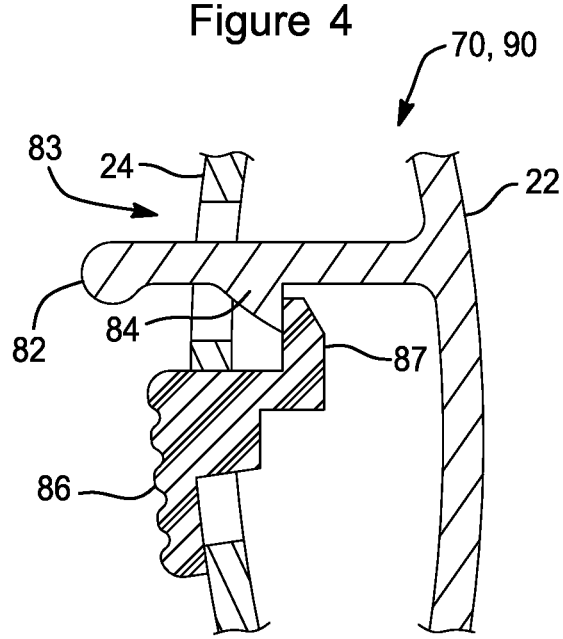
FIG. 5 illustrates an electrosurgical device with a selectable securing mechanism.

FIG. 5 illustrates a close up view of a securing mechanism 70 which as shown is also an arm securing mechanism 90 that secures the first working arm 22 and the second working arm together 24. The first working arm 22 includes a resilient tongue 82 with a tongue 84 that protrudes off of one side of the resilient tongue 82. The second working arm 24 includes a slot 83 that the resilient tongue 82 extends into. The second working arm 24 includes a latch slider 86 that locks the first working arm 22 and the second working arm 24 together. The latch slider 86 includes a front end 87 that extends outward and contacts the tongue 84 of the resilient tongue 82. The latch slider 86 and the tongue 84 both include a flat portion that when moved into contact prevent the first working arm 22 and second working arm 24 from being separated. The latch slider 86 can be moved along the longitudinal axis of the working arms to release the tongue 84 so that the working arms are again movable relative to each other.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A device comprising:
   forceps including:
   i. a first working arm; and
   ii. a second working arm;
   a blade;
   an arm securing mechanism comprising a first slider operably connected to the first working arm and second working arm and slidable along a longitudinal axis of the device between at least a first position where the first working arm and second working arm are free to move in a direction towards each other to grasp tissue therebetween and a second position that secures the first working arm and second working arm in a fixed relationship to one another; and a blade extending mechanism comprising a second slider connected to the blade and slidable along the longitudinal axis of the device between a plurality of slider positions where the blade is locked into a position corresponding to each of the plurality of slider positions;

wherein the device is configured to be switchable, during a surgical procedure, between:

A. a first mechanical configuration where the first slider is in the first position and the first working arm and second working arm are free to move in the direction towards each other to grasp tissue therebetween, and the blade is locked, via the second slider of the blade extending mechanism, into a position corresponding to a first one of the plurality of slider positions;

B. a second mechanical configuration where the first slider is in the second position and the first working arm and second working arm are secured together preventing movement of the first working arm and the second working arm in the direction towards each other; and C. a third mechanical configuration where the first slider is in the second position and the first working arm and second working arm are fixedly secured in relationship to one another, and the blade is locked, via the second slider of the blade extending mechanism, into a position corresponding to a second one of the plurality of slider positions so that the blade is substantially flush with or extends beyond a distal end of the first working arm and the second working arm.

2. The device of claim 1, wherein each of the plurality of slider positions comprises a detent locking the second slider in the corresponding slider position.

3. The device of claim 1, wherein the device includes a shuttle that connects the first slider and the second slider.

4. The device of claim 3, wherein the device includes a bias device that moves, the first slider, the second slider, the blade, or a combination thereof in a fully extended position, substantially flush position, a partially extended position, a fully retracted position, or a combination thereof.

5. The device of claim 4, wherein the bias device is a spring, an elastomer piece, a detent, or a combination thereof.

6. The device of claim 1, wherein the blade in the first mechanical configuration is retracted so that a distal end of the blade is located proximal of the first working arm and the second working arm.

7. The device of claim 1, wherein the blade in the second mechanical configuration is retracted so that a distal end of the blade is located proximal of the first working arm and the second working arm.

8. The device of claim 1, wherein the blade is substantially flush with the distal end of the first working arm and the second working arm in the third configuration, and wherein the device is configured to be further switchable into a fourth mechanical configuration where the first slider is in the second position and the first working arm and second working arm are fixedly secured in relationship to one another, and the blade extends beyond the first working arm and the second working arm.

9. The device of claim 8, wherein the first working arm and the second working arm extend on opposing sides of the blade and grip the blade in the third mechanical configuration and in the fourth mechanical configuration.

10. The device of claim 9, wherein, in the third mechanical configuration and the fourth mechanical configuration, the first working arm and the second working arm contact opposing sides of the blade so that the blade is prevented from moving relative to the first working arm and the second working arm.

11. The device of claim 1 wherein:

the arm securing mechanism comprises a selectively engageable electromagnetic latch; and the first working arm and second working arm are biased towards each other by a force when the electromagnetic latch is activated and energized.

12. The device of claim 1, wherein the blade is substantially flush with the distal end of the first working arm and the second working arm in the third configuration, and wherein the device is configured to be further switchable into a fourth mechanical configuration where the first slider is in the second position and the first working arm and second working arm are fixedly secured in relationship to one another, and the blade is locked, via the second slider of the blade extending mechanism, into a position corresponding to a third one of the plurality of slider positions so that the blade extends beyond the first working arm and the second working arm.

13. A device comprising:

a forceps including:
 i. a first working arm; and
 ii. a second working arm;

a blade;

an arm securing mechanism comprising a first slider operably connected to the first working arm and second working arm and slidable along a longitudinal axis of the device between at least a first position where the first working arm and second working arm are free to move in a direction towards each other to grasp tissue therebetween and a second position that secures the first working arm and second working arm in a fixed relationship to one another; and a blade extending mechanism comprising a second slider connected to the blade and slidable along the longitudinal axis of the device between a plurality of slider positions where the blade is locked into a position corresponding to each of the plurality of slider positions;

wherein the device is configured to be switchable, during a surgical procedure, between:

a first mechanical configuration where the first slider is in the first position and the first working arm and second working arm are free to move in the direction towards each other so as to grasp tissue therebetween, and the blade is locked, via the second slider of the blade extending mechanism, into a position corresponding to a first one of the plurality of slider positions;

a second mechanical configuration where the first slider is in the second position and, the first working arm and second working arm are fixedly secured in relationship to one another, and the blade is locked, via the second slider of the blade extending mechanism, into a position corresponding to a second one of the plurality of slider positions so that the blade is extended by the blade extending mechanism to be flush with a distal end of the working arms; and a third mechanical configuration wherein the first slider is in the second position and the first working arm and second working arm are fixedly secured in relationship to one another, and the blade is extended by the blade extending mechanism to extend beyond the distal end of the working arms.

14. The device of claim 13, wherein the device is configured to be further switchable into a fourth mechanical configuration where the first slider is in the second position and the first working arm and second working arm are secured together to prevent movement of the first working arm and the second working arm in the direction towards or a direction away from each other, and the blade is locked into the position corresponding to the first one of the plurality of slider positions.

15. The device of claim 13, wherein, in the second mechanical configuration and the third mechanical configuration, the first working arm and the second working arm contact opposing sides of the blade so that the blade is prevented from moving relative to the first working arm and the second working arm.

16. The device of claim 13, wherein the device includes a bias device that moves the first slider, the second slider, the blade, or a combination thereof to a fully extended position, a substantially flush position, a partially extended position, a fully retracted position, or a combination thereof.

17. The device of claim 16, wherein the bias device is a spring, an elastomer piece, a detent, or a combination thereof.

18. The device of claim 13, wherein in the third mechanical configuration, the blade is locked, via the second slider of the blade extending mechanism, into a position corresponding to a third one of the plurality of slider positions.

19. A device comprising:
   forceps including:
      i. a first working arm; and
      ii. a second working arm;
   a blade;
   an arm securing mechanism connected to the first working arm and second working arm and moveable between at least a first position where the first working arm and second working arm are free to move in a direction towards each other to grasp tissue therebetween and a second position preventing movement of the first working arm and the second working arm in a direction away from each other; and
   a blade extending mechanism connected to the blade and configured for movement along a longitudinal axis of the device to position the blade in each of a plurality of blade positions;
   wherein the device is configured to be switchable, during a surgical procedure, between:
      a first mechanical configuration where the arm securing mechanism is in the first position and the first working arm and second working arm are free to move in the direction towards each other to grasp tissue therebetween, and the blade is positioned, via the blade extending mechanism, into a first one of the plurality of blade positions;
      a second mechanical configuration where the arm securing mechanism is in the second position, preventing movement of the first working arm and second working arm in the direction away from each other; and
      a third mechanical configuration where the arm securing mechanism is in the second position, preventing movement of the first working arm and second working arm in the direction away from each other, and the blade is positioned, via the blade extending mechanism, into a second one of the plurality of blade positions so that the blade is substantially flush with or extends beyond a distal end of the first working arm and the second working arm; and
   wherein movement of the blade extending mechanism in a distal direction causes movement of the arm securing mechanism into the second position preventing movement of the first working arm and the second working arm in the direction away from each other.

20. The device of claim 19, wherein the arm securing mechanism comprises a pair of opposing immobilization arms, a first one of the immobilization arms being connected to the first working arm and extending in an opposite direction of the first working arm, and a second one of the immobilization arms being connected to the second working arm and extending in an opposite direction of the second working arm.

* * * * *

UNITED STATES PATENT AND TRADEMARK OFFICE
CERTIFICATE OF CORRECTION

PATENT NO. : 10,898,260 B2
APPLICATION NO. : 16/219197
DATED : January 26, 2021
INVENTOR(S) : Batchelor et al.

Page 1 of 1

It is certified that error appears in the above-identified patent and that said Letters Patent is hereby corrected as shown below:

On the Title Page

Item (71), in "Applicant", in Column 1, Line 1, delete "INC.," and insert --INC. D/B/A Olympus Surgical Technologies America,-- therefor Item (73), in "Assignee", in Column 1, Line 1, delete "Inc.," and insert --Inc. d/b/a Olympus Surgical Technologies America,-- therefor Item (57), in "Abstract", in Column 2, Line 1, delete "a a" and insert --a-- therefor On page 4, in Column 2, item (56) under "Other Publications", Line 24, delete "2104" and insert --2014-- therefor On page 5, in Column 2, item (56) under "Other Publications", Line 7, delete "PCT/US2015/045850m" and insert --PCT/US2015/045850,-- therefor In the Claims In Column 23, Line 42, in Claim 4, delete "moves," and insert --moves-- therefor In Column 24, Line 58, in Claim 13, delete "and," and insert --and-- therefor Signed and Sealed this
Twentieth Day of April, 2021

Drew Hirshfeld
*Performing the Functions and Duties of the
Under Secretary of Commerce for Intellectual Property and
Director of the United States Patent and Trademark Office*